United States Patent
Mittal et al.

(10) Patent No.: US 9,737,276 B2
(45) Date of Patent: *Aug. 22, 2017

(54) METHOD FOR ESTIMATING FLOW RATES, PRESSURE GRADIENTS, CORONARY FLOW RESERVE, AND FRACTIONAL FLOW RESERVE FROM PATIENT SPECIFIC COMPUTED TOMOGRAPHY ANGIOGRAM-BASED CONTRAST DISTRIBUTION DATA

(71) Applicant: The Johns Hopkins University, Baltimore, MD (US)

(72) Inventors: Rajat Mittal, Vienna, VA (US); Albert C. Lardo, Baldwin, MD (US); Jung Hee Seo, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 185 days.

This patent is subject to a terminal disclaimer.

(21) Appl. No.: 14/189,380

(22) Filed: Feb. 25, 2014

(65) Prior Publication Data
US 2014/0187928 A1    Jul. 3, 2014

Related U.S. Application Data

(63) Continuation of application No. 13/868,697, filed on Apr. 23, 2013, now Pat. No. 9,320,487.

(Continued)

(51) Int. Cl.
*A61B 5/05*    (2006.01)
*A61B 6/00*    (2006.01)
(Continued)

(52) U.S. Cl.
CPC ............ *A61B 6/507* (2013.01); *A61B 5/0044* (2013.01); *A61B 5/026* (2013.01);
(Continued)

(58) Field of Classification Search
USPC ....... 600/410, 425, 438, 454, 458, 468, 504; 703/9
See application file for complete search history.

(56) References Cited

U.S. PATENT DOCUMENTS

2006/0098852 A1 *  5/2006  Omi ...................... A61B 5/026
                                                            382/128
2006/0206032 A1    9/2006  Miele et al.
(Continued)

FOREIGN PATENT DOCUMENTS

WO          0121057 A2      3/2001

OTHER PUBLICATIONS

Wintermark et al. ("The Anterior cerebral artery is an appropriate arterial input function for perfusion-CT processing in patients with acute stroke", Published in Diagnostic Neuroradiology, No. 50, Dec. 5, 2007, pp. 227-236).*

(Continued)

*Primary Examiner* — James Kish
(74) *Attorney, Agent, or Firm* — Johns Hopkins Technology Ventures

(57) ABSTRACT

An embodiment in accordance with the present invention provides a method for non-invasively determining the functional severity of coronary artery stenosis. The method includes gathering patient-specific data related to concentration of a contrast agent within a coronary artery of a patient using a coronary computed tomography angiography scan (CCTA). The patient-specific data is used to calculate a patient-specific transluminal attenuation gradient for the coronary artery of the patient. The patient specific transluminal attenuation gradient is used to determine an estimate of a coronary flow velocity, pressure gradient, loss coefficient, coronary flow reserve, and/or fractional flow reserve for the patient. Coronary flow velocity, pressure gradient, loss coefficient, coronary flow reserve, and fractional flow (Continued)

reserve can then be used to estimate the functional severity of coronary artery stenosis.

25 Claims, 20 Drawing Sheets

Related U.S. Application Data

(60) Provisional application No. 61/705,422, filed on Sep. 25, 2012.

(51) Int. Cl.
    *A61B 6/03*         (2006.01)
    *A61B 5/02*         (2006.01)
    *A61B 5/00*         (2006.01)
    *A61B 5/026*       (2006.01)
    *G06T 7/00*         (2017.01)

(52) U.S. Cl.
    CPC ............ *A61B 5/02007* (2013.01); *A61B 6/03* (2013.01); *A61B 6/032* (2013.01); *A61B 6/481* (2013.01); *A61B 6/503* (2013.01); *A61B 6/504* (2013.01); *A61B 6/5205* (2013.01); *A61B 6/5217* (2013.01); *G06T 7/0016* (2013.01); *F04C 2270/041* (2013.01); *G06T 2207/10076* (2013.01); *G06T 2207/10081* (2013.01); *G06T 2207/30076* (2013.01); *G06T 2207/30104* (2013.01)

(56) References Cited

U.S. PATENT DOCUMENTS

| | | | |
|---|---|---|---|
| 2007/0019778 A1* | 1/2007 | Clouse et al. | 378/4 |
| 2010/0234698 A1 | 9/2010 | Manstrom et al. | |
| 2010/0241000 A1 | 9/2010 | Kondo et al. | |
| 2011/0085977 A1* | 4/2011 | Rosenmeier | 424/9.1 |
| 2012/0150516 A1* | 6/2012 | Taylor et al. | 703/9 |

OTHER PUBLICATIONS

Choi, J., et al., "Intracoronary transluminal attenuation gradient in coronary CT angiography for determining coronary artery stenosis", JACC: Cardiovascular Imaging, vol. 4, No. 11, Nov. 1, 2011, pp. 1149-1157.

International Search Report and Written Opinion, mailed Aug. 23, 2013; PCT/US2013/037804 filed Apr. 24, 2013.

* cited by examiner

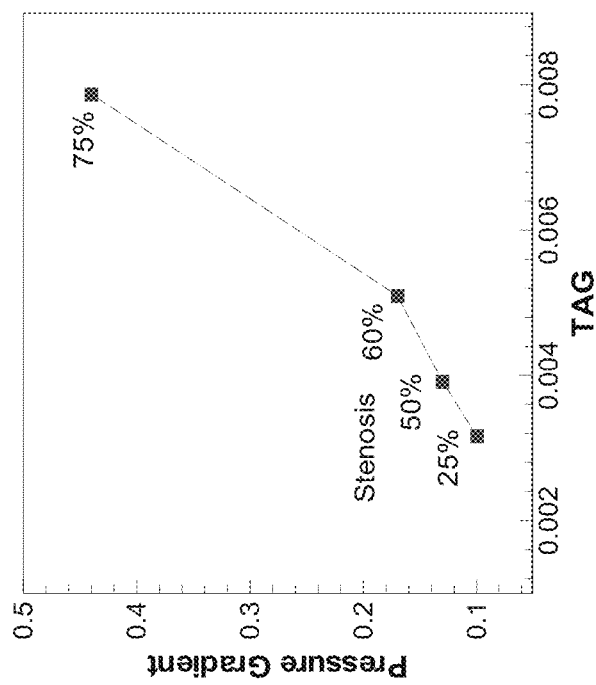
FIG. 2D
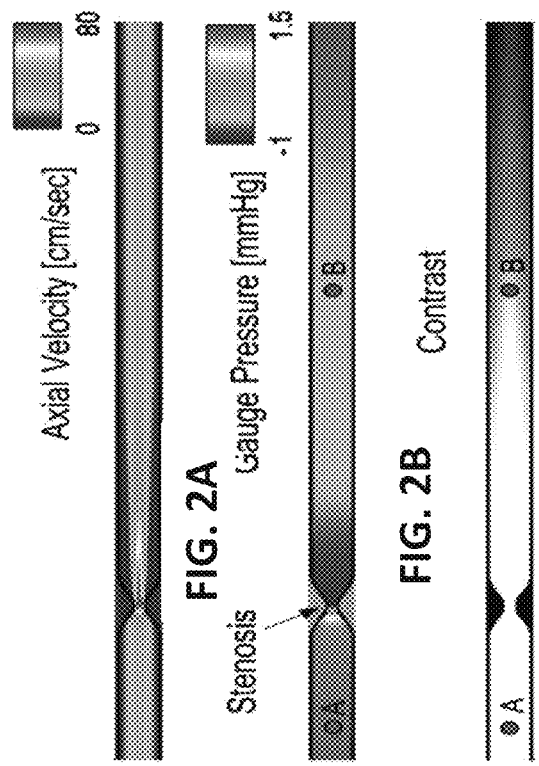
FIG. 2A
FIG. 2B
FIG. 2C

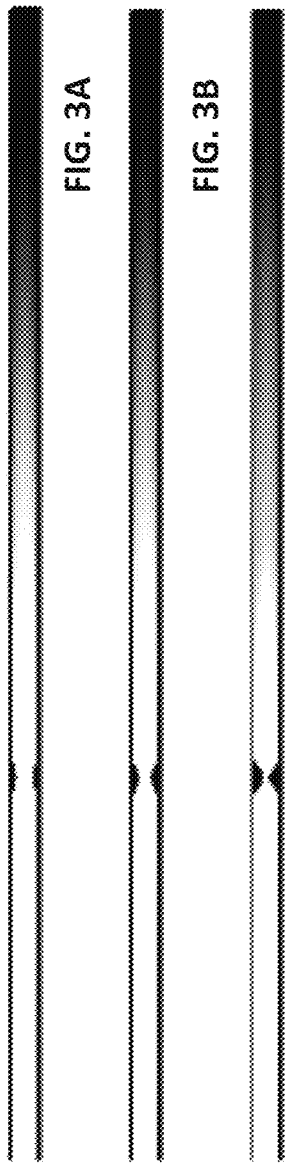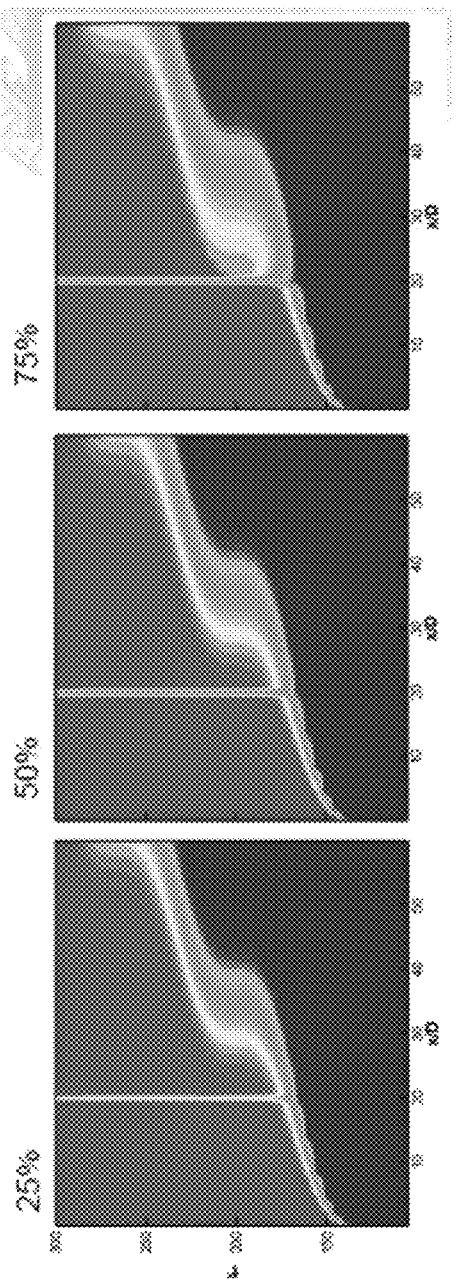
FIG. 3A
FIG. 3B
FIG. 3C
FIG. 3D
FIG. 3E
FIG. 3F
$Re = 200, St = 0.015, Wo = 1.88$

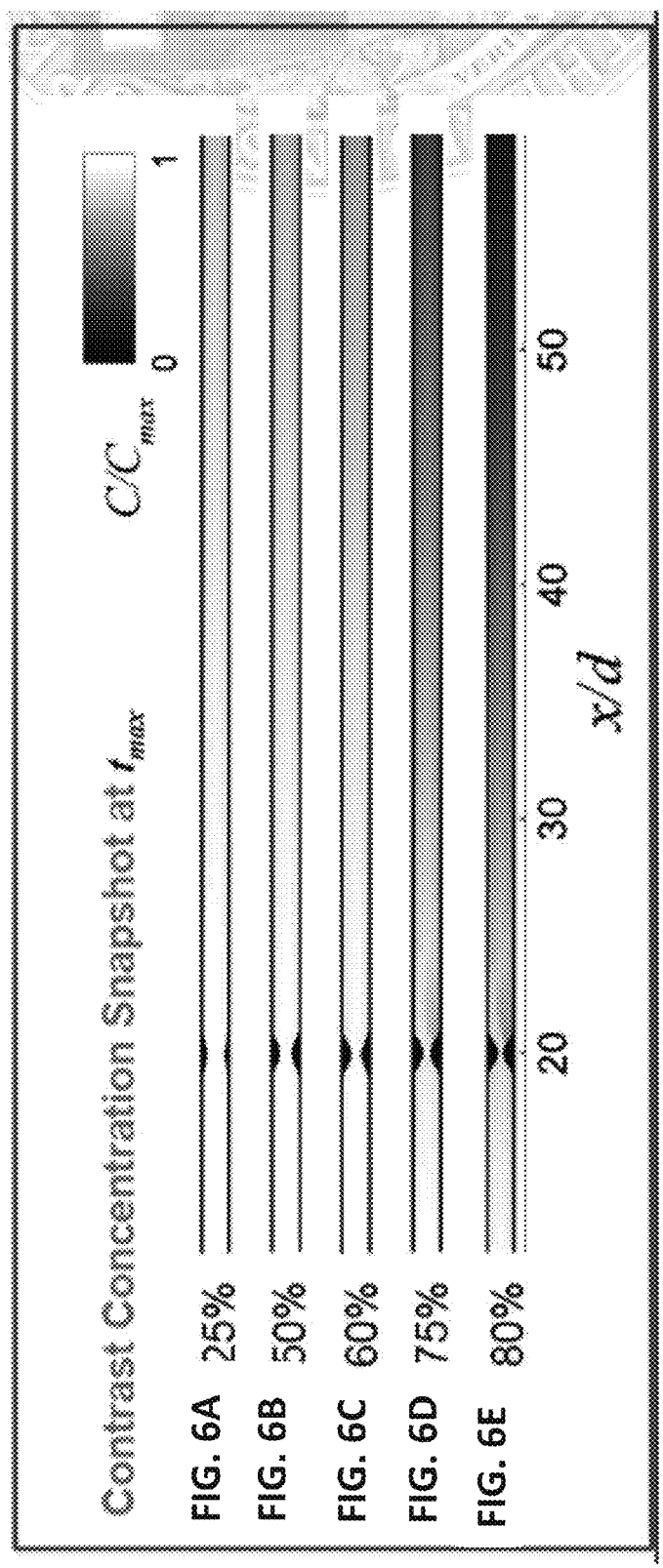

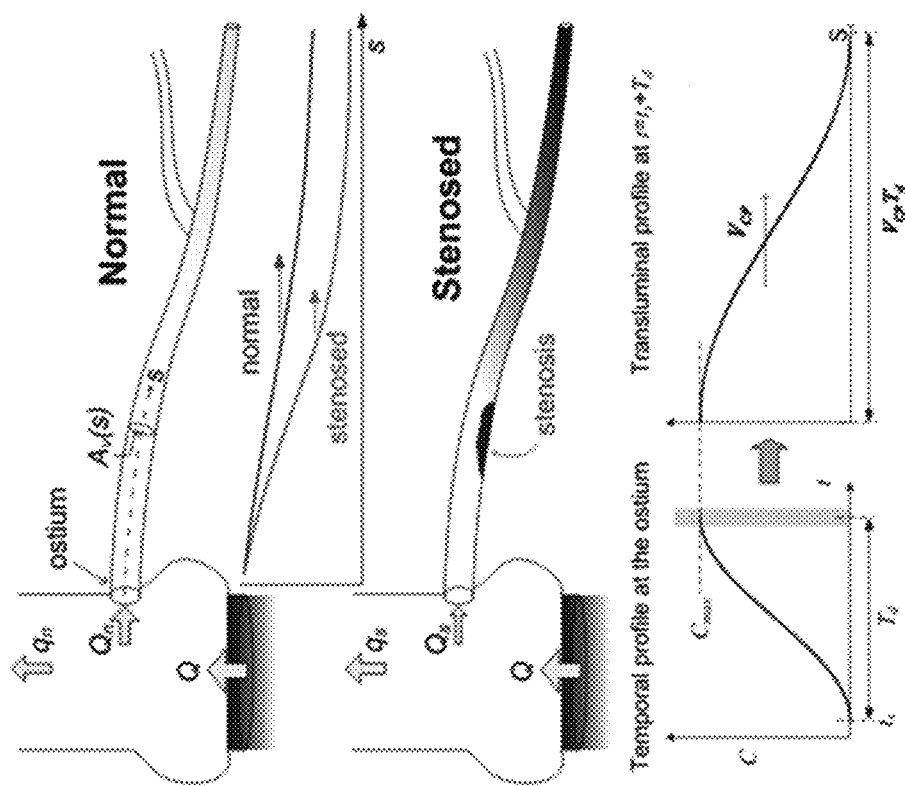

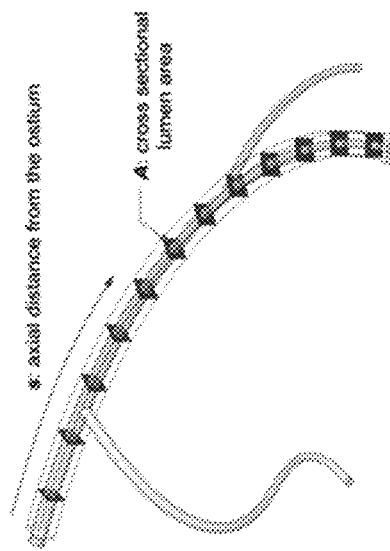
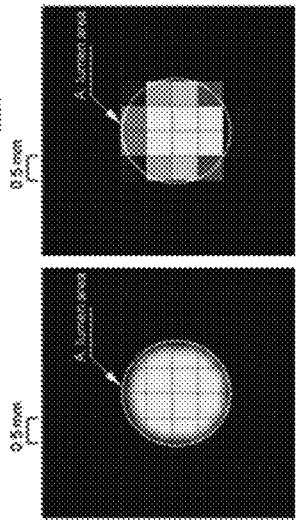
FIG. 13A
FIG. 13B
FIG. 13C
FIG. 13D

US 9,737,276 B2

METHOD FOR ESTIMATING FLOW RATES, PRESSURE GRADIENTS, CORONARY FLOW RESERVE, AND FRACTIONAL FLOW RESERVE FROM PATIENT SPECIFIC COMPUTED TOMOGRAPHY ANGIOGRAM-BASED CONTRAST DISTRIBUTION DATA

CROSS REFERENCE TO RELATED APPLICATIONS

This application is a continuation of U.S. patent application Ser. No. 13/868,697 filed on Apr. 23, 2013, which claims the benefit of U.S. Provisional Patent Application No. 61/705,422 filed on Sep. 25, 2012, and International Application No. PCT/US2013/037804 filed on Apr. 23, 2013, all of which are incorporated by reference, herein, in their entirety.

FIELD OF THE INVENTION

The present invention relates generally to cardiology. More particularly, the present invention relates to a computed tomography cardiac imaging based method for determining flow rates, pressure gradients and coronary and fractional flow reserve.

BACKGROUND OF THE INVENTION

The coronary arteries supply the myocardium, or muscle of the heart with oxygen and nutrients. Over time the coronary arteries can become blocked with cholesterol and other material known as plaque. Coronary artery disease results from this buildup of plaque within the walls of the coronary arteries. Excessive plaque build-up can lead to diminished blood flow through the coronary arteries and blow blood flow to the myocardium leading to chest pain, ischemia, and heart attack. Coronary artery disease can also weaken the heart muscle and contribute to heart failure, a condition where the heart's efficiency as a pump is compromised. This state can lead to electrical disorders of the heart that increase the possibility for sudden cardiac death. Coronary artery is the leading cause of death for both men and women in the United States.

There are several different diagnostics that are currently used to assess coronary artery disease and its severity. Non-invasive tests can include electrocardiograms, biomarker evaluations from blood tests, treadmill tests, echocardiography, single positron emission computed tomography (SPECT), and positron emission tomography (PET). Unfortunately, these non-invasive tests do not provide data related to the size of a coronary lesion or its specific effect on coronary blood flow, lesion pressure gradients and fractional flow reserve.

While CT scans and MRI can be used to visualize the size of the lesion, lesion size does not necessarily correlate to the functional significance of the lesion. Therefore, additional assessments have been developed to determine functional significance of coronary artery lesions. Generally, coronary flow velocity (CFV), pressure gradient (PG), coronary flow reserve (CFR), and fractional flow reserve (FFR) are the gold standard for assessments used to determine the functional significance of coronary artery stenosis. These metrics are currently determined using diagnostic cardiac catheterization, a procedure in which a catheter is inserted into an artery in a patient's leg and threaded through the vasculature to the relevant areas of the coronary arteries. FFR is determined by calculating the ratio of the mean blood pressure downstream from a lesion divided by the mean blood pressure upstream from the same lesion. These pressures are measured by inserting a pressure wire into the patient during the diagnostic cardiac catheterization procedure. While this procedure provides an accurate measure of FFR for determining the functional severity of the coronary stenosis, it is only obtained after the risk and cost of an invasive procedure have already been assumed.

FFR can also be estimated based on a highly complex computational fluid dynamics modeling in CT derived, patient-specific coronary models. This approach requires a high level of sophistication, is computationally expensive, and requires that patient-specific data be transmitted out of the hospital environment to a third party vendor. It is expensive and can take several days to obtain results. Additionally, recent data testing this approach to predict actual FFR in a multicenter trial were very disappointing.

It would therefore be advantageous to provide an alternative non-invasive CT based method for assessing hemodynamic parameters such as determining the CFV, PG, CFR, and/or FFR for a given patient's coronary arteries. Such an approach would fundamentally change the practice of clinical cardiology and allow clinicians to clearly identify specific vessels that are resulting in a reduction in the blood flow to the myocardium.

SUMMARY OF THE INVENTION

The foregoing needs are met, to a great extent, by the present invention, wherein in one aspect a method for determining a functional significance of coronary artery stenosis includes obtaining a patient specific transluminal attenuation gradient (TAG) (also called transluminal contrast gradient TCG) for the coronary artery of the patient and determining contrast concentration versus time data at a predetermined location such as in the left ventricular chamber or coronary artery or aorta of the patient. Such curves are defined as the arterial input function (AIF). The AIF is measured immediately following the injection of contrast by a dynamic CT protocol that is typically used to monitor contrast concentration in the heart or blood vessel to optimally time the CT acquisition of the heart. Once the monitoring is complete, the CT scanner stops AIF collection to begin CT acquisition of the heart.

The method provides a mathematical relationship between spatial dispersion of contrast in the coronary vessels (TAG, TCG) and temporal contrast dispersion of the AIF. Such a relationship allows the calculation of coronary flow velocity (CFV) within the artery using the TAG and the AIF and using the CFV along with the vessel cross sectional area to calculate flow and determine the functional significance of the coronary artery stenosis. The CFV can be determined at rest as well as stress to generate an estimate of the coronary flow reserve (CFR) which provides a measure of the functional significance of the lesion. CFV may be estimated in the branches of the main artery under consideration and provide the relative distribution of flow rate in these branches. This information may also be used to determine the functional significant of the coronary lesion.

In accordance with another aspect of the present invention, a method for determining a functional significance of coronary artery stenosis includes obtaining a patient specific transluminal attenuation gradient (TAG) for the coronary artery of the patient and determining a time variation of a contrast at a predetermined location in the left ventricular blood pool cavity, ascending or descending aorta, coronary artery of the patient or any other vascular location (called the arterial input function or input bolus profile). The method also includes calculating an estimate of the pressure gradient (PG) within the coronary artery using the relationship between TAG and AIF. PG is then used to determine the functional significance of the coronary artery stenosis through the estimation of the loss coefficient (K) associated with the stenotic lesion. Unlike FFR, characterization of the functional significance of the stenoses through K does not require a second measurement in stress condition.

In accordance with another aspect of the present invention, the method can include gathering patient-specific data related to the spatial concentration of a contrast agent within a coronary artery of a patient at a given time (TAG). This patient specific data can be gathered under rest or stress conditions. Although the use of the estimation of the loss coefficient (K) can be used to eliminate the need for data gathered under stress. The patient-specific data can be used to calculate the patient-specific TAG for the coronary artery of the patient. In addition, the method can be executed using a computer readable medium. The patient-specific data is represented as a graph of concentration of the contrast agent over a distance in the coronary artery.

In accordance with another aspect of the present invention, a method for determining a functional significance of coronary artery stenosis includes obtaining a patient specific transluminal attenuation gradient (TAG) for the coronary artery of the patient and determining a time variation of a contrast at a predetermined location vascular or ventricular location (called the arterial input function or input bolus profile). The method also includes calculating an estimate of the fractional flow reserve (FFR) within the coronary artery using the TAG and AIF and using the FFR to determine the functional significance of the coronary artery stenosis.

In accordance with yet another aspect of the present invention, the method can include gathering patient-specific data related to concentration of a contrast agent within a coronary artery of a patient. The patient-specific data can be used to calculate the patient-specific TAG for the coronary artery of the patient. In addition, the method can be executed using a computer readable medium. A cardiac computed tomography scan can be used to gather the patient specific TAG. The patient-specific data is represented as a graph of concentration of the contrast agent over a distance in the coronary artery. The TAG and AIF can also be used to calculate PG and a loss coefficient in order to determine the functional significance of the coronary artery stenosis.

In accordance with another aspect of the present invention, a method for determining the functional significance of coronary artery stenosis in patients with severe calcifications is described and includes a method for obtaining a patient specific transluminal attenuation gradient (TAG) over a calcium-free section of the coronary artery and determining a time variation of a contrast at a predetermined location vascular or ventricular location (called the arterial input function or input bolus profile). The method also includes calculating an estimate of the fractional flow reserve (FFR) within the coronary artery using the TAG and AIF and using the FFR to determine the functional significance of the coronary artery stenosis in vessels with severe calcification.

In accordance with another aspect of the present invention, a method for determining the functional significance of coronary artery stenosis includes obtaining a patient specific transluminal attenuation gradient (TAG) for the coronary artery of the patient and determining a time variation of a contrast at a predetermined vascular or ventricular location (called the arterial input function or input bolus profile). The method also includes calculating an estimate of the fractional flow reserve (FFR) and flow within the coronary artery using the TAG and AIF and using the FFR to determine the functional significance of the coronary artery stenosis. The technique also includes a method for correcting the TAG values for the effects of CT spatial resolution and partial volume averaging.

In accordance with another aspect of the present invention, a method for determining the functional significance of coronary artery stenosis includes obtaining a patient specific transluminal attenuation gradient (TAG) for the coronary artery of the patient and determining a time variation of a contrast at a predetermined location vascular or ventricular location (called the arterial input function or input bolus profile). The method also includes calculating an estimate of the fractional flow reserve (FFR) and flow within the coronary artery using the TAG and AIF and using the FFR to determine the functional significance of the coronary artery stenosis. The technique also includes a method for correcting the TAG values for the effects of vessel tortuosity, curvature and partial volume averaging.

In accordance with another aspect of the present invention, a method for determining a functional significance of coronary artery stenosis includes obtaining coronary contrast concentration versus time data via a dynamic CT acquisition to calculate coronary flow velocity.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIGS. 2A-2C illustrate schematic diagrams of axial velocity, gauge pressure, and contrast dispersion, respectively, according to an embodiment of the invention.

FIG. 2D illustrates the relationship between transarterial gradient (TAG) and the pressure gradient within the vessel for data points at 25%, 50%, 60%, and 75% stenosed, respectively, according to an embodiment of the invention.

FIGS. 3A-C illustrate the dispersion of contrast in the coronary artery through contrast graphs depicting spatiotemporal evolution of contrast in the symmetrically constricted coronary arteries, according to an embodiment of the invention.

FIGS. 3D-F illustrate the concentration of the contrast at different distances (x/D) along the coronary artery over time ($t^*$) for coronary arteries having 25%, 50%, and 75% symmetric constriction, respectively, according to an embodiment of the invention.

FIGS. 6A-6E illustrate schematic diagrams of contrast dispersion in a blood vessel having 25%, 50%, 60%, 75%, and 80% symmetric constriction, respectively, according to an embodiment of the invention.

FIGS. 12A-12C illustrate aspects related to TAG in normal and stenosed vessels according to an embodiment of the present invention.

FIGS. 13A-13D illustrate a method for assessing partial volume averaging effect from CFD data, according to an embodiment of the present invention.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a method for non-invasively determining the functional severity of coronary artery stenosis. The method includes gathering patient-specific data related to concentration of a contrast agent within a coronary artery of a patient using a coronary computed tomography angiography scan (CCTA). The patient specific data can be gathered from rest or under stress. Although the use of the estimation of a loss coefficient (K) can be used to eliminate the need for data gathered under stress. The patient-specific data is used to calculate a patient-specific transluminal attenuation gradient for the coronary artery of the patient. The data may be corrected for imaging artifacts at any stage of the analysis. The patient specific transluminal attenuation gradient is used to determine an estimate of the coronary flow velocity, pressure gradient, coronary flow reserve, and/or fractional flow reserve for the patient. Coronary flow velocity, pressure gradient, coronary flow reserve, and fractional flow reserve can then be used to estimate the functional severity of coronary artery stenosis.

Figure 1A:
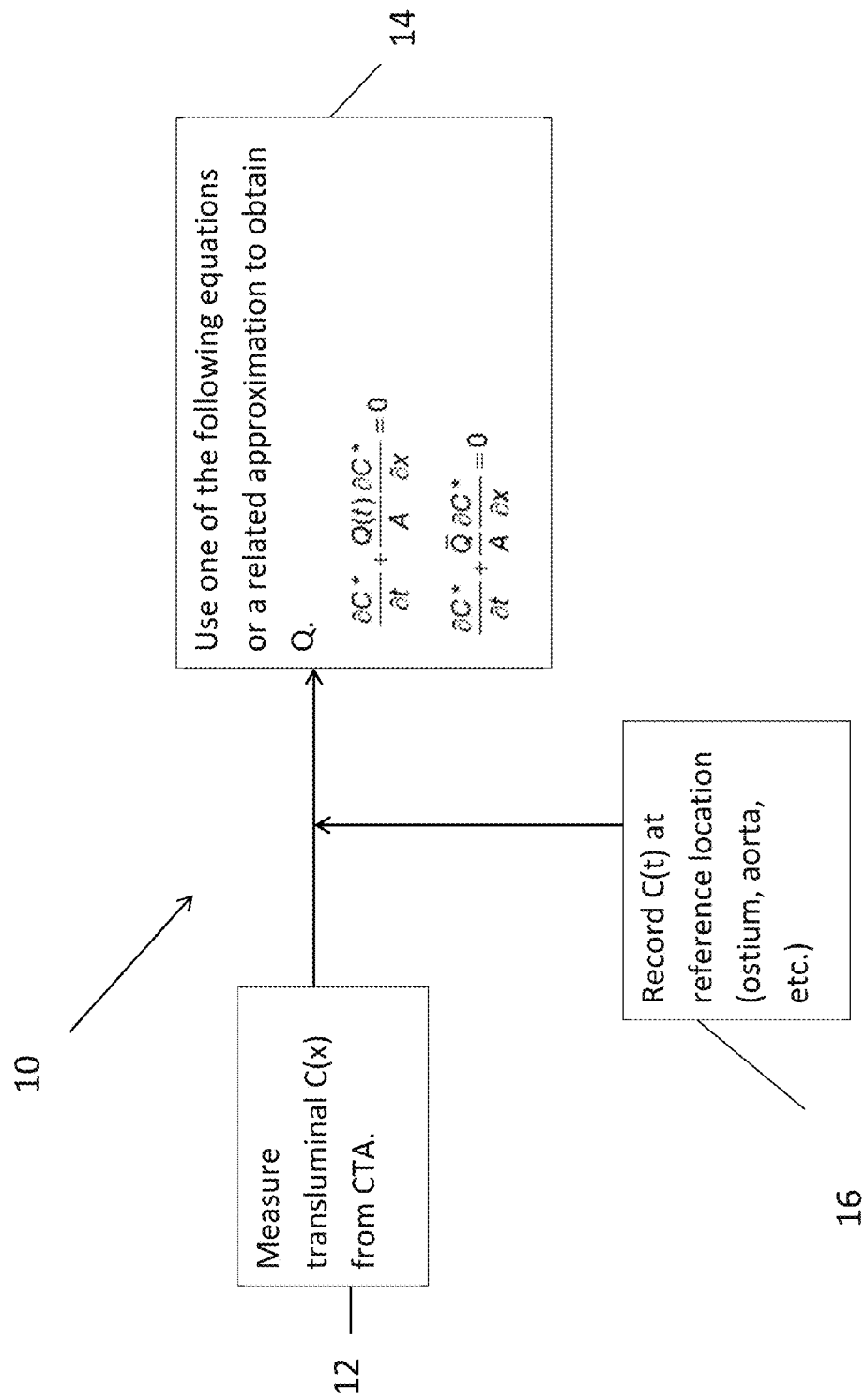
FIG. 1A illustrates a flow diagram of a method of determining the functional severity of coronary artery constriction, according to an embodiment of the invention.
Figure 1B:
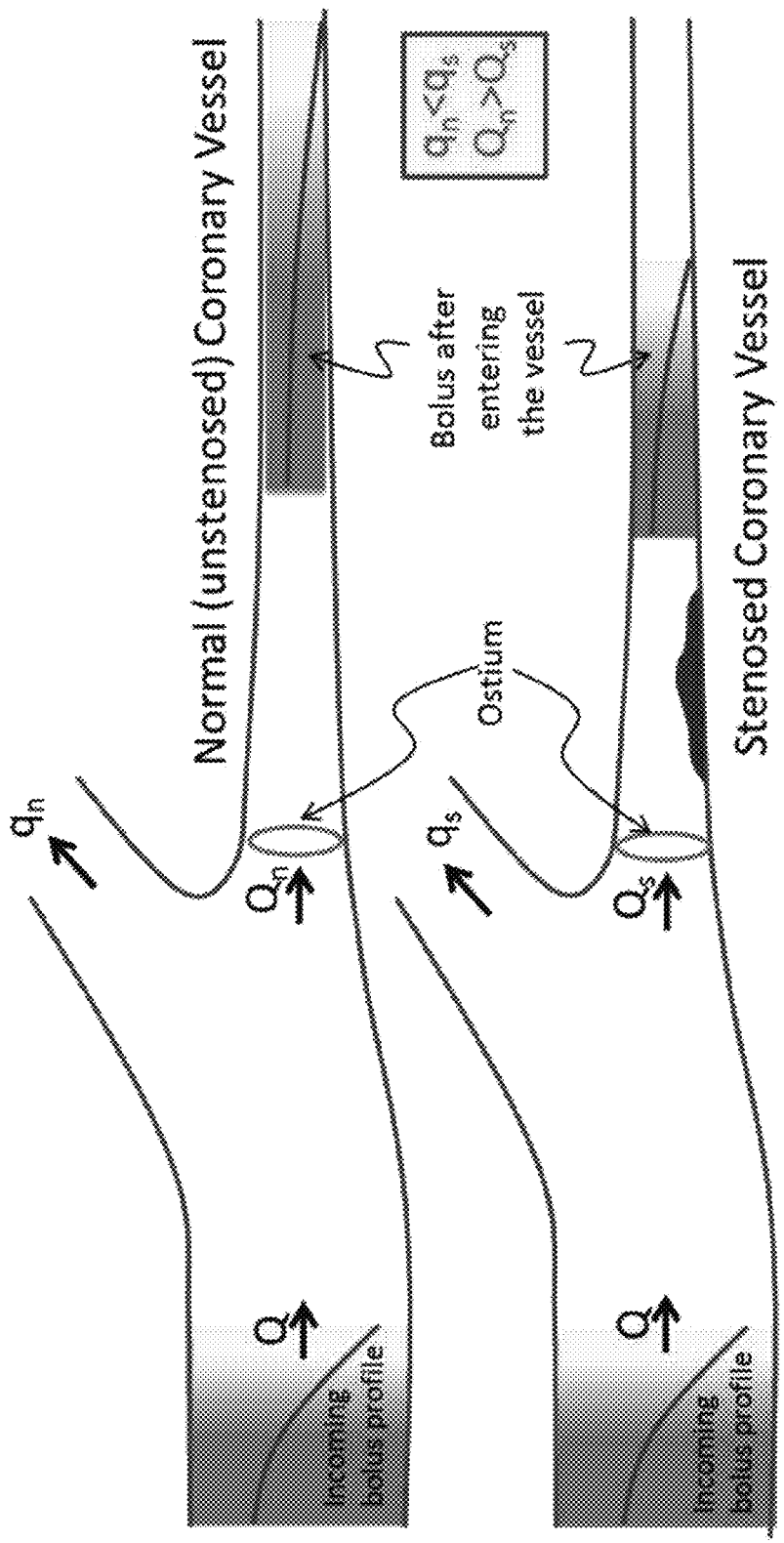
FIG. 1B illustrates the convection of the bolus into a coronary artery and how the presence of a stenosis will change the TAG.

FIG. 1A illustrates a flow diagram of a method 10 of determining the functional severity of coronary artery constriction, according to an embodiment of the invention. The method includes a step 12 of obtaining patient specific contrast CTA data on an artery of interest and measuring the transluminal C(x). CTA scans are routinely acquired during angiography and myocardial perfusion scans. Therefore, in most cases the data can be obtained without requiring an additional procedure or scan. This allows physicians and diagnosticians to reduce invasive procedures for patients, as well as reduce the patients' exposure to radiation and contrast dye. Any suitable CT scanner known to one of skill in the art can be used. It is also expected that as medical imaging technology progresses, additional medical imaging devices currently in development or that will be developed in the future could also be used to execute the method. FIG. 1B shows the overall concept of the convection of the bolus into a coronary artery and how the presence of a stenosis will change the TAG.

With respect to the method illustrated in FIG. 1A, in one embodiment, an arterial input function (AIF) is measure immediately following the injection of a contrast by a dynamic CT protocol that is typically used to monitor contrast concentration in the heart or blood vessel to optimally time the CT acquisition of the heart. Once the monitoring is complete, the CT scanner stops AIF collection to begin CT acquisitions of the heart. Thereby, the method provides a mathematical relationship between the spatial dispersion of contrast in the coronary vessels (TAG, TCG) and temporal contrast dispersion of the AIF. Such a relationship allows the calculation of coronary flow velocity (CFV) within the artery using the TAG and the AIF and using the CFV along with the vessel cross sectional area to calculate flow and determine the functional significance of the coronary artery stenosis. The CFV can be determined at rest as well as stress to generate an estimate of the coronary flow reserve (CFR) which provides a measure of the functional significance of the lesion. CFV may be estimated in the branches of the main artery under consideration and provide the relative distribution of flow rate in these branches. This information may also be used to determine the functional significant of the coronary lesion.

An example of patient specific data from the CTA scan that can be used in conjunction with the method described herein is data illustrating the dispersion of a contrast agent in a coronary artery over time. It should be noted, however, the concentration of the contrast can be measured at predetermined locations in the left ventricular blood pool cavity, ascending or descending aorta, coronary artery of the patient, or any other vascular location. Other data known to one of skill in the art could, however, also be used to execute the method described herein. FIGS. 2A-2C illustrate schematic diagrams of axial velocity, gauge pressure, and contrast dispersion, respectively. The exemplary data in FIGS. 2A-2C is derived from a computer model having a Reynolds Number (Re) of 200, Strouhal number (St) of 0.015, and Womersley number (W0) of 1.88. However, similar results would be obtained from a human patient.

FIG. 2D further illustrates the relationship between transluminal attenuation gradient (TAG) and the pressure gradient within the vessel for data points at 25%, 50%, 60%, and 75% stenosed, respectively. The graph represents the correlation between non-dimensionalized trans-stenotic pressure and contrast gradients (TCG) between points A and B, as illustrated in FIGS. 2A-2C. The method of correlating pressure and TAG is discussed further below.

FIGS. 3A-C further illustrate the dispersion of contrast in the coronary artery through contrast graphs depicting spatio-temporal evolution of contrast in the symmetrically constricted coronary arteries. The graphs in FIGS. 3D-F illustrate the concentration of the contrast at different distances (x/D) along the coronary artery over time (t*) for coronary arteries having 25%, 50%, and 75% symmetric constriction, respectively. The spike in each of the graphs at x/D=20 represents the stenosis.

Figure 3G:
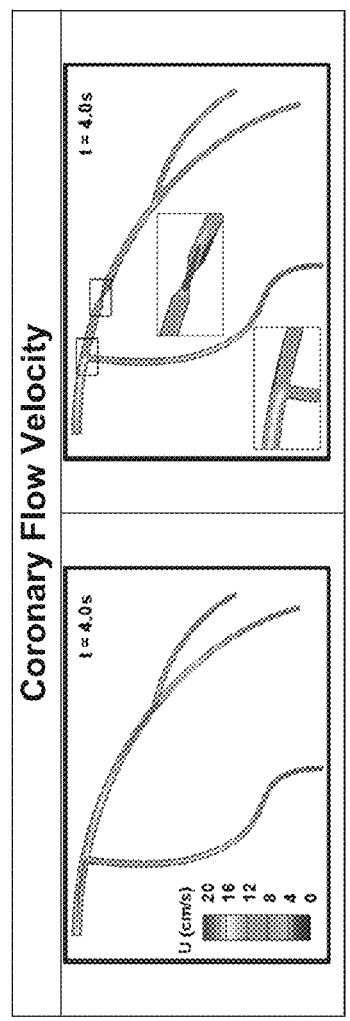
FIG. 3G illustrates the coronary flow velocity between models of normal and stenosed arteries respectively, according to an embodiment of the invention.
Figure 3H:
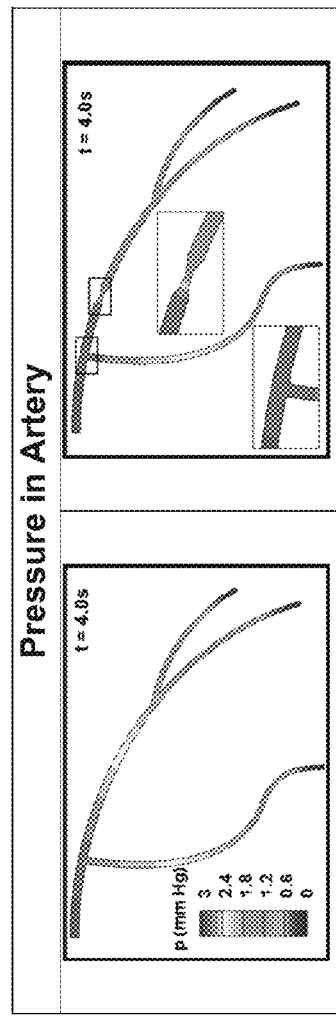
FIG. 3H illustrates the coronary pressure comparison between models of normal and stenosed arteries respectively, according to an embodiment of the invention.

FIG. 3G illustrates the coronary flow velocity between models of normal and stenosed arteries respectively, according to an embodiment of the invention. FIG. 3H illustrates the coronary pressure comparison between models of normal and stenosed arteries respectively, according to an embodiment of the invention.

Figures 4A, 4B:
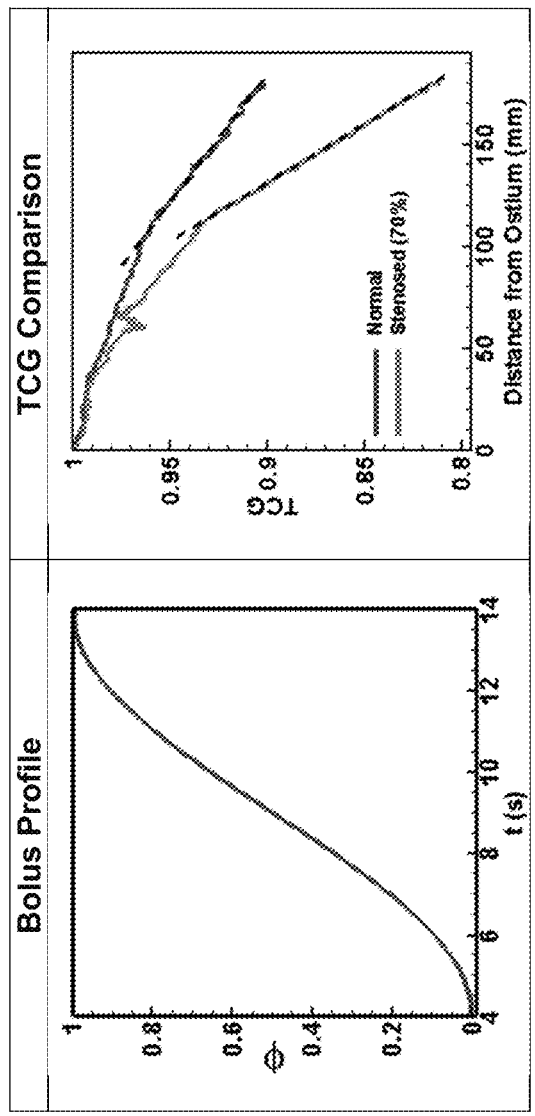
FIG. 4A illustrates a graph plotting the arterial input function (or input bolus profile) provided at the inlet of the computational modeling procedure according to an embodiment of the invention.
FIG. 4B illustrates the TAG values estimated for the two models according to an embodiment of the invention.

FIG. 4A illustrates a graph plotting the arterial input function (AIF or input bolus profile) provided at the inlet of the computational modeling procedure according to an embodiment of the invention. AIF includes obtaining a patient specific TAG for the coronary artery of the patient and determining a time variation of a contrast at a predetermined location in the left ventricular blood pool cavity, ascending or descending aorta, coronary artery of the patient or any other vascular location. The method provides a mathematical relationship between spatial dispersion of contrast in the coronary vessels (TAG, TCG) and temporal contrast dispersion of the AIF. Such a relationship allows the calculation of coronary flow velocity (CFV) within the artery using the TAG and the AIF and using the CFV along with the vessel cross sectional area to calculate flow and determine the functional significance of the coronary artery stenosis. The CFV can be determined at rest as well as stress to generate an estimate of the coronary flow reserve (CFR) which provides a measure of the functional significance of the lesion. CFV may be estimated in the branches of the main artery under consideration and provide the relative distribution of flow rate in these branches. This information may also be used to determine the functional significant of the coronary lesion. FIG. 4B illustrates the TAG values estimated for the two models according to an embodiment of the invention.

Figure 5:
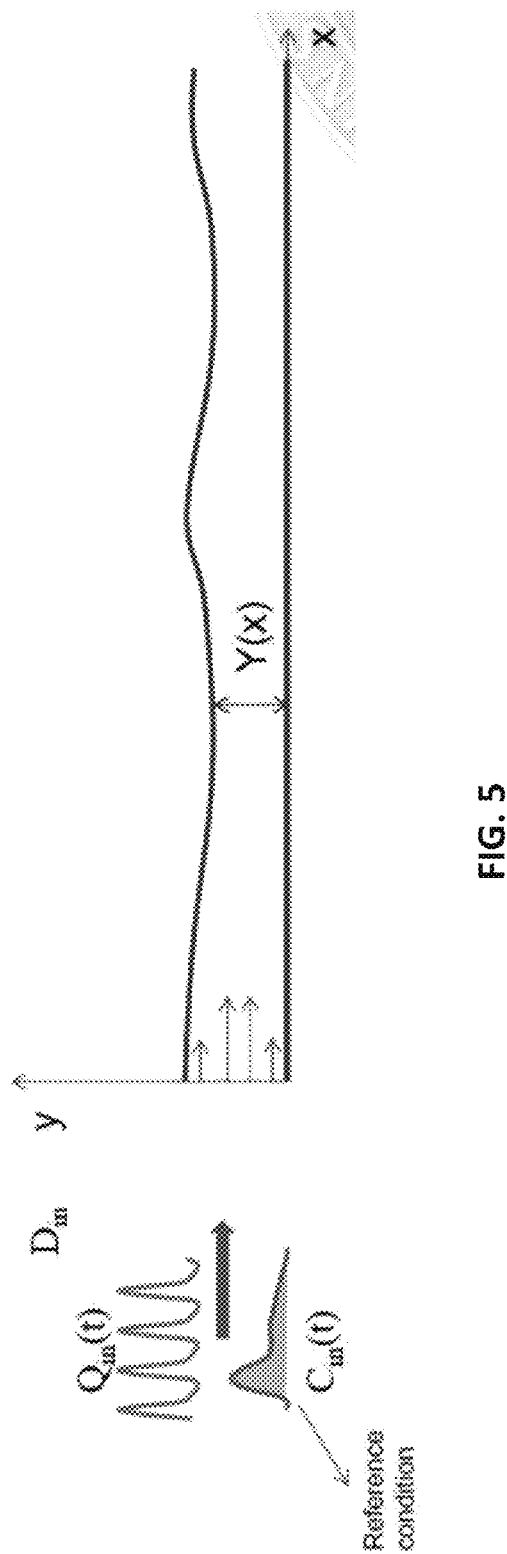
FIG. 5 illustrates a schematic that explains the typical conditions for a coronary artery.

FIG. 5 illustrates a schematic which depicts the typical situation of blood flow and contrast dispersion in an artery. Q is the incoming flow rate to the artery and $C_{in}$ is the arterial input function of the contrast. From the graph Equation (1) for streamwise velocity and Equations (2) and (3) for contrast, are derived, and reproduced below. Note, these equations are shown for a two-dimensional situation, to simplify description. Equations (1), (2), and (3) can also be extended to more realistic arterial geometries known to one of skill in the art.

$$\frac{\partial u}{\partial t} + \frac{\partial (uu)}{\partial x} + \frac{\partial (vu)}{\partial y} = -\frac{1}{\rho}\frac{\partial p}{\partial x} + \frac{\mu}{\rho}\left(\frac{\partial^2 u}{\partial x^2} + \frac{\partial^2 u}{\partial y^2}\right) \quad (1)$$

$$\frac{\partial c}{\partial t} + \frac{\partial (uc)}{\partial x} + \frac{\partial (vc)}{\partial y} = -\frac{D}{\rho}\left(\frac{\partial^2 c}{\partial x^2} + \frac{\partial^2 c}{\partial y^2}\right) \quad (2)$$

$$\frac{\partial u}{\partial x} + \frac{\partial v}{\partial y} = 0 \quad (3)$$

Solving Equation (4) provides the definition of section integrated quantity:

$$\int_{Y(x)} f(x,y)\,dy = \bar{f}(x) \quad (4)$$

Note: $\int_{Y(x)} u(x,y)\,dy = \bar{u} = Q = \text{flow rate}$ (5)

where Q is another quantity of interest for a non-invasive CTA base assessment of flow rate at rest and stress, useful for estimating the functional significance of a stenosis. Additionally, note:

$$\int_{Y(x)} c(x,y)\,dy = C \propto HU \quad (6A)$$

where HU denotes the CTA measurement of the opacification in terms of Haunsfeld Units. Equations 1, 2, and 3 can also be section integrated, as shown, below:

Eq. (1)

$$Q_t = \int_{T(x)} (uu)_x\,dy + \int (vu)\,dy =$$

$$-\frac{1}{\rho}\frac{\partial \bar{p}}{\partial x} + \frac{\mu}{\rho}\int_{Y(x)} \frac{\partial^2 u}{\partial x^2}\,dy + [\tau_w(Y) - \tau_w(0)] \quad (6B)$$

Eq. (2)

$$\frac{\partial C}{\partial t} + \int_{Y(x)} (uc)_x\,dy + \int (vc)\,dy =$$

$$\frac{D}{\rho}\int_{Y(x)} \frac{\partial^2 c}{\partial x^2}\,dy + \frac{D}{\rho}\,\xi(Y) - \xi(0)$$

Eq. (3)

$$\frac{\partial Q}{\partial x} = 0 \Rightarrow Q = Q(t)$$

FIGS. 6A-6E illustrate schematic diagrams of contrast dispersion in a blood vessel having 25%, 50%, 60%, 75%, and 80% symmetric constriction, respectively. The arterial input function (or input bolus profile) for these models at the arterial ostium is shown in FIG. 6F and this is similar to the input function in actual measurements. As illustrated in FIGS. 6A-6E the contrast disperses farther along the blood vessel only having a 25% constriction than in the blood vessel having 50%, 60%, 75%, or 80% constriction. The exemplary data in FIGS. 6A-6E is derived from a computer model having a Reynolds Number (Re) of 200, Strouhal number (St) of 0.015, and Womersely number of (Wo) of 1.88. However, similar results would be obtained from a human patient. Equations (7) and (8), are alternative versions of Eq. 6B which is more suitable for further analysis $$\frac{\partial \vec{U}}{\partial t} + (\vec{U} \cdot \nabla)\vec{U} + \frac{\nabla P}{\rho_0} = v_0 \nabla^2 \vec{U}, \nabla \cdot \vec{U} = 0 \qquad (7)$$

$$\frac{\partial C}{\partial t} + (\vec{U} \cdot \nabla)C = D\nabla^2 C \qquad (8)$$

Figure 6F:
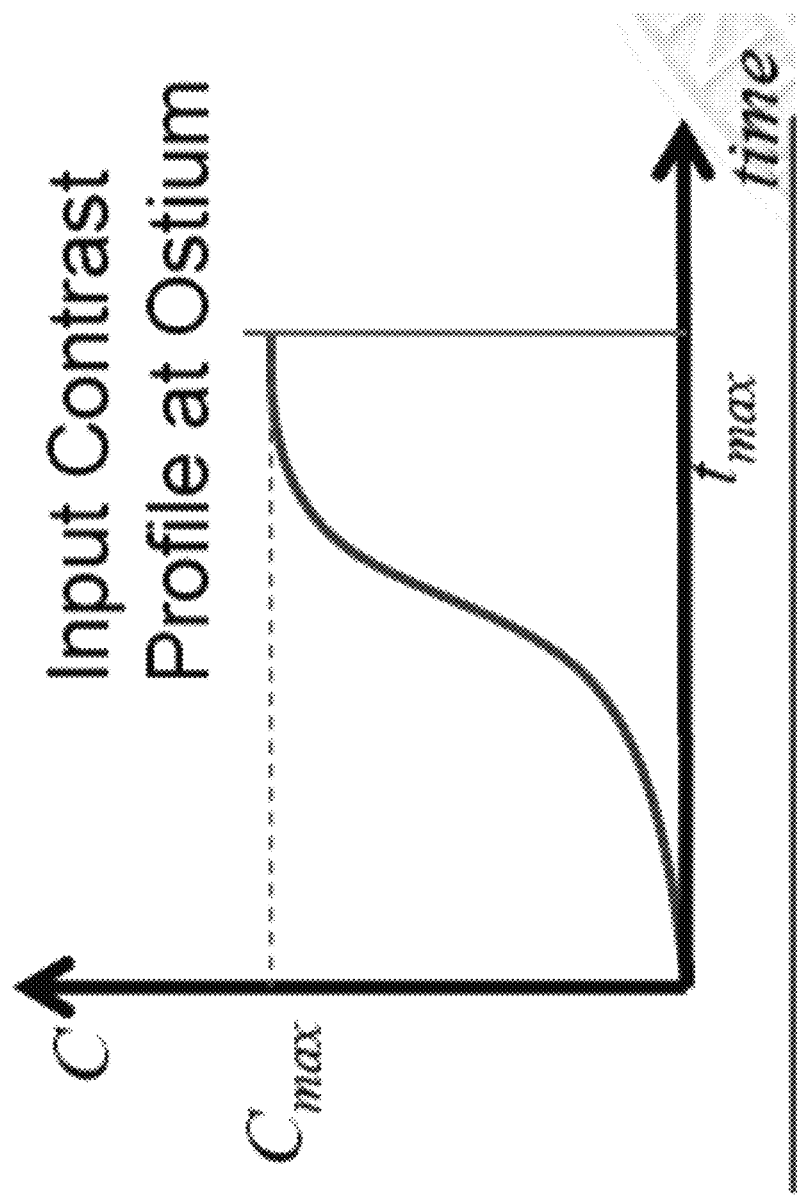
FIG. 6F illustrates a graph showing the input contrast profile at the ostium, over time "t", according to an embodiment of the invention.

FIG. 6F illustrates a graph showing the input contrast profile at the ostium, over time "t".

Figures 7A, 7B:
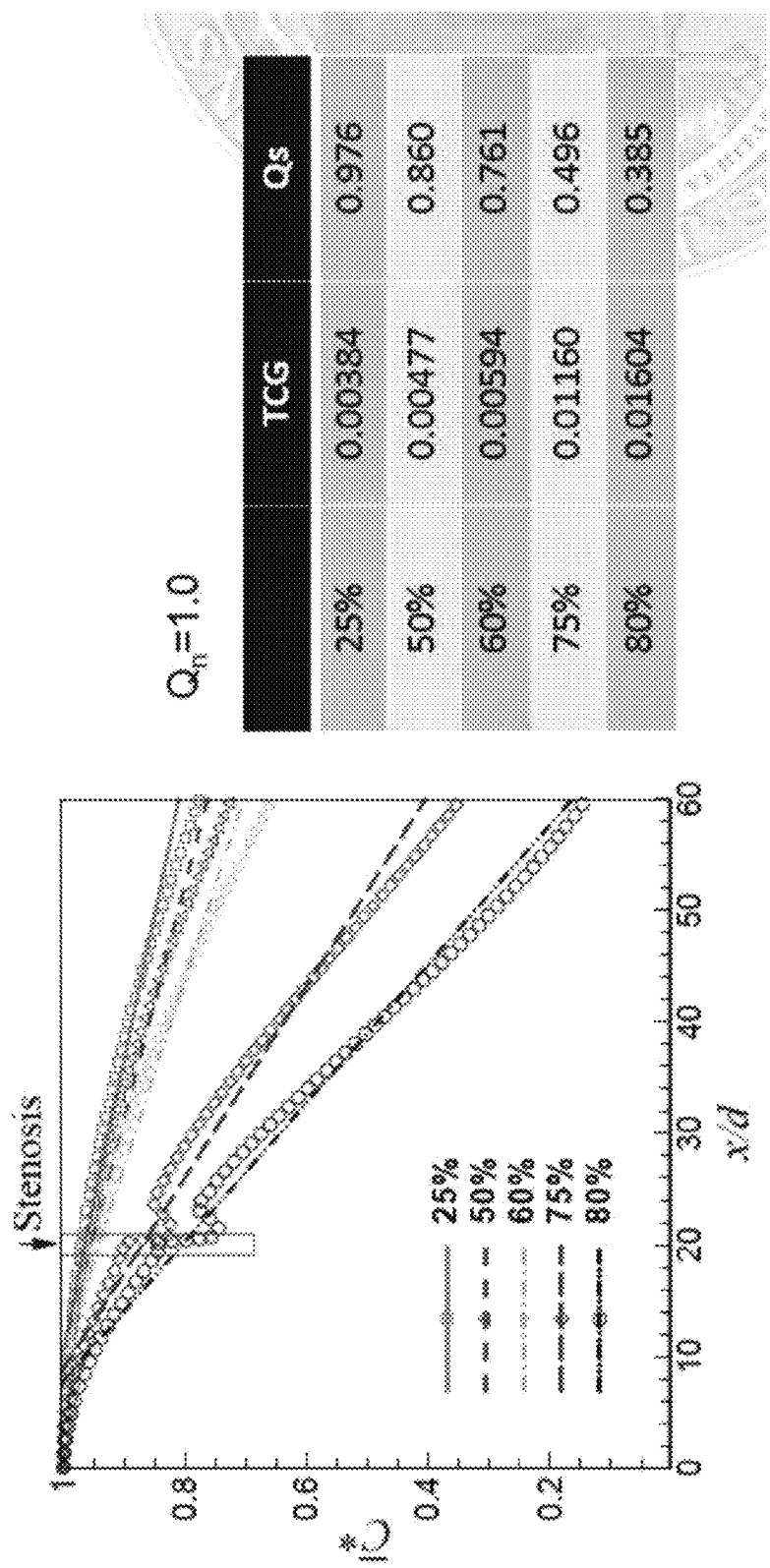
FIG. 7A illustrates a graph of an area averaged and normalized contrast profile.
FIG. 7B illustrates a table of Q values for different values of TCG (or TAG) according to an embodiment of the invention.

FIG. 7A illustrates a graph of an area averaged and normalized contrast profile. Contrast dispersion over distance and time is measured for 25%, 50%, 60%, 75%, and 80% constriction. FIG. 7A further illustrates a transluminal contrast profile for the cross sectional averaged and normalized concentration within the blood vessel. The graphed lines are least squares, fitting to the linear function ax+b. It should also be noted that TCG=−a. Equation (9) represents the area averaged and normalized contrast profile.

$$\overline{C}*(x, t) = \frac{\int C(x, y, t) dy}{A(x) \cdot C_{max}} \qquad (9)$$

FIG. 7B illustrates a table of TCG values for different values of Q. This clearly illustrates that there is direct correlation between TAG and flow rate (Q).

Figure 8B:
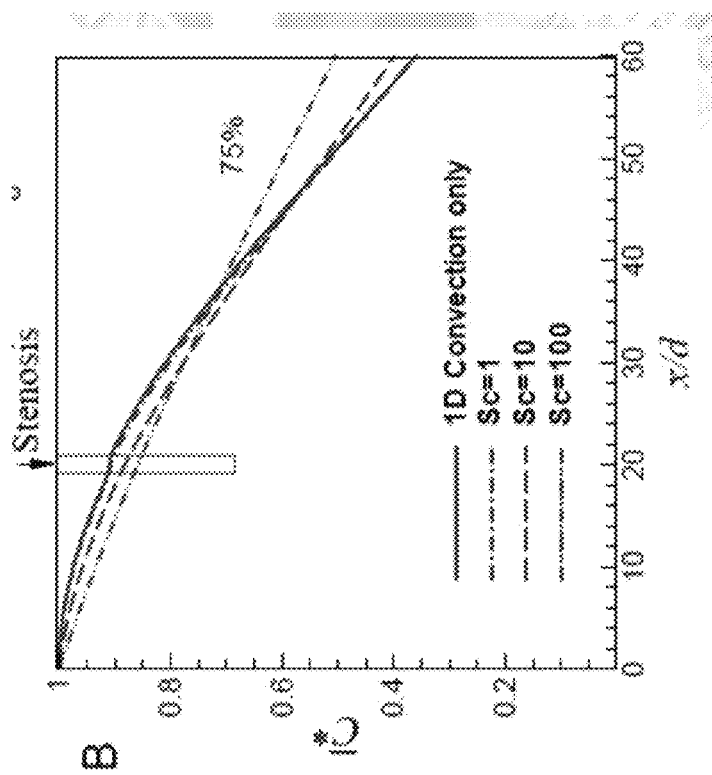
FIG. 8B illustrates a graphical views of the transluminal contrast profile for different contrast agents.
Figure 8A:
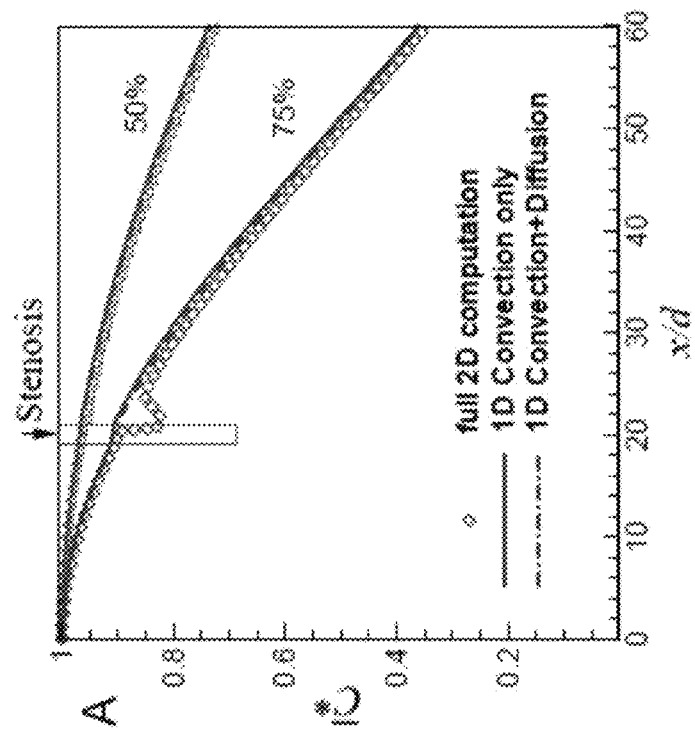
FIG. 8A illustrates a graphical views of the transluminal contrast profile for two different stenoses and compares TCG computed from full flow model with simple one-dimensional convection and convection-diffusion equations.

FIG. 8A shows that the contrast dispersion pattern and TAG can be represented quite accurately by simplified one-dimensional models. This model can be written as follows $$\left(\frac{\partial}{\partial t} + \overline{U}\frac{\partial}{\partial x}\right)\overline{C}^* = \left(D + \frac{d^2\overline{U}^2}{BD}\right)\frac{\partial^2 \overline{C}^*}{\partial x^2} \qquad (10)$$

$$\overline{U} = \int U dy/A = Q/A \qquad (11)$$

where B is associated with Taylor dispersion and B=210 for a 2D channel and 192 for a circular pipe. The figure also shows that further simplifications are possible by eliminating the diffusion term of Eq. (10) without significantly affecting the prediction of TAG. This is important since simplified equations can be solved very rapidly without the need for powerful computers. This is a key advantage of the current method over CFD based estimation of FFR.

FIG. 8B illustrates graphical views of the transluminal contrast profile predicted by the one dimensional cross-sectional averaged equation, Equation (10) and (11) below. FIG. 8B illustrates the effect of diffusivity (Schmidt Number) of the contrast agent.

Figure 9:
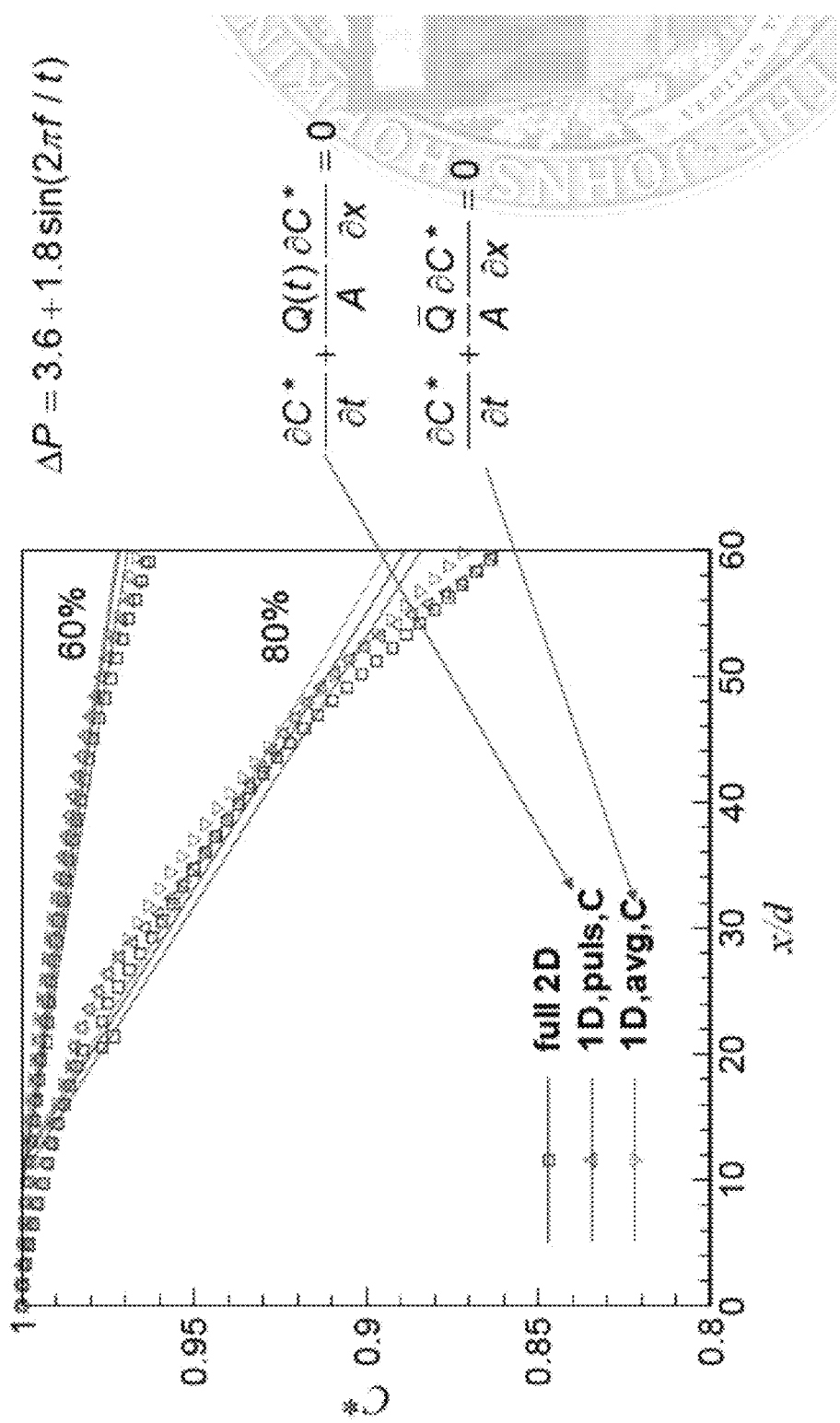
FIG. 9 illustrates a graph plotting contrast dispersion over distance for pulsatile flow, according to an embodiment of the invention.

FIG. 9 illustrates a graph plotting contrast dispersion over distance for cases where flow pulsatility is considered. Actual arterial flows are pulsatile and this data is intended to show that the basis features of the TCG-velocity correlation are not affected by flow pulsatility. One curve represents a full two-dimensional model. Another represents a one-dimensional model of pulsatile flow, and another represents an even simpler model of one-dimensional flow which employs time-averaged flow velocity. This figure shows that linear TAG is still present flow despite pulsatility in the flow.

Figure 10:
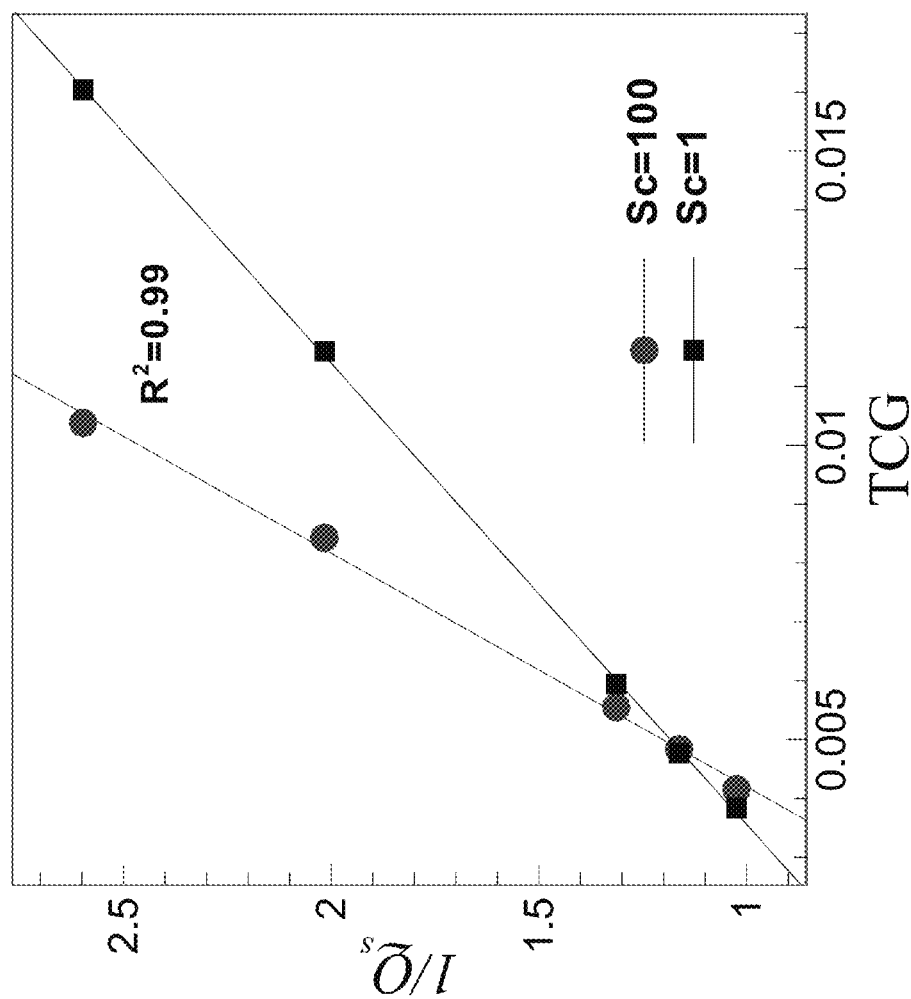
FIG. 10 illustrates the correlation between flow rate and TCG, according to an embodiment of the invention.

FIG. 10 illustrates the correlation between flow rate and TCG. Here flow rate is graphed as the inverse of stenosed flow rate, or $1/Q_s$. TCG can therefore be used to extract the flow rate in the artery. Q can be estimated using Equation (12) or (13). Further, Equations (14), (15), and (16) can be used to estimate flow rate, velocity, and pressure gradient. It should however be noted that these equations are merely included as examples and the velocity, flow rate, and pressure gradient can also be estimated using other mathematical approximations known to those of skill in the art.

$$\frac{\partial C^*}{\partial t} + \frac{Q(t)}{A}\frac{\partial C^*}{\partial x} = 0 \qquad (12)$$

$$\frac{\partial C^*}{\partial t} + \frac{\overline{Q}}{A}\frac{\partial C^*}{\partial x} = 0 \qquad (13)$$

$$\int_{Y(x)} (uc)_x dy = \frac{D}{\rho}\overline{c}_{xx} - C_t \Rightarrow \overline{u} \qquad (14)$$

$$= \frac{D}{\rho C}\int_x \overline{c}_{xx} dx - \int_{Y(x)} (u'c') dy$$

$$\int_{Y(x)} u(x, y) dy = \overline{u} = Q = \text{flow rate} \qquad (15)$$

$$\frac{\partial \overline{p}}{\partial x} = -\rho\left\{Q_t - \int_{Y(x)} (uu)_x dy + \frac{\mu}{\rho}\overline{u}_{xx} + [\tau_w(Y) - \tau_w(0)]\right\} \qquad (16)$$

Figure 11:
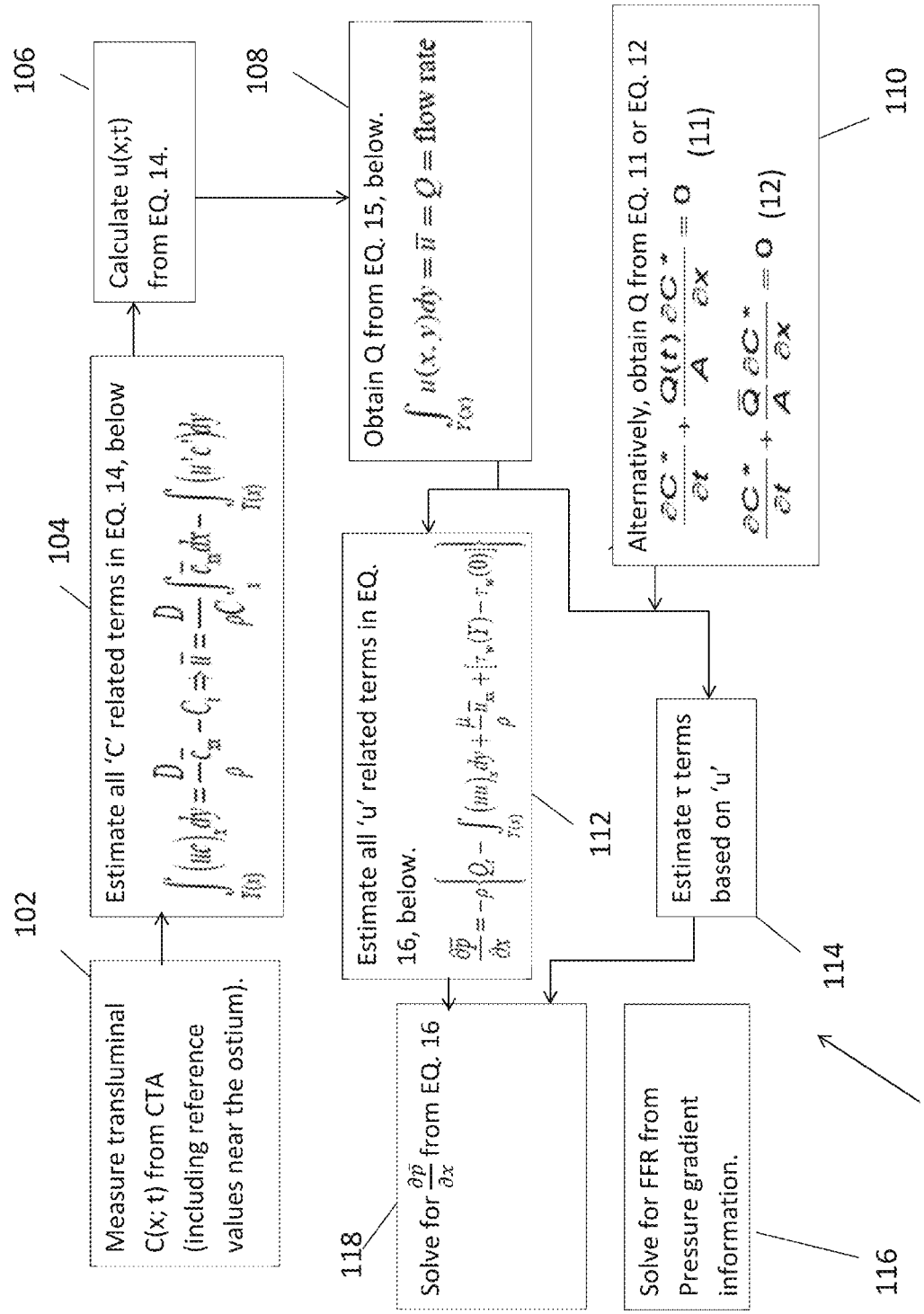
FIG. 11 illustrates a method 100 with a step 102 of measuring transluminal C(x, t) from CTA, including the reference values near the ostium, according to an embodiment of the invention.

FIG. 1 further illustrates step 14 incorporating the procedures described above, and using Equations (12) or (13) to approximate Q. In step 16, C(t) can be recorded at a reference location (i.e. the arterial input function), such as the ostium or aorta, and then used in the calculation to approximate Q. FIG. 11 expands on the method of FIG. 1. FIG. 11 illustrates a method 100 with a step 102 of measuring transluminal C(x, t) from CTA, including the reference values near the ostium. Step 104 includes estimating all C related terms in Equation (14), and step 106 includes calculating u(x, t) from Equation (14), or an approximation thereof. Step 108 includes obtaining a value for Q from Equation (15). Alternately step 110 can be used and Q can be estimated from Equation (12) or Equation (13). Step 112 includes estimating all u terms in Equation (16), and step 114 includes estimating tau terms based on the value for u. Pressure gradient is solved for in step 116 from Equation (16) and FFR is solved for in step 118 from the pressure gradient calculation. These steps can be carried out for a given patient in rest and stressed conditions and the flow rate and/or pressure information obtained from these two conditions provides another measure of functional significance of the stenosis. These steps can also be carried out using a computer, computer readable medium, or alternately a computing device incorporated into the CT scanner. Indeed, any suitable method of calculation known to or conceivable by one of skill in the art could be used.

FIGS. 12A-12C illustrate TAG in normal and stenosed vessels. More particularly, FIG. 12A illustrates a schematic diagram of TAG in a normal (top) and stenosed (bottom) vessel, showing a concentration distribution of luminal iodine (white to black). Note the increased gradient (decreasing axial concentration) in the stenosed vessel. According to the present invention, the axial contrast gradient is generated by the advection of the temporally varying iodine concentration at the coronary ostium, using the arterial input function, as illustrated in FIG. 12C. TAG is an instantaneous spatial measurement of this advective effect, as illustrated in FIG. 12B. This critically important relationship between TAG and temporal contrast dispersion patterns can be used to decode local hemodynamics and allow direct calculation of coronary flow during a standard CTA exam. The challenge of the mathematical formulation is to relate a "snapshot" of the static measurement of iodine concentration along the vessel length (TAG) and dynamic iodine concentration changes following intravenous injection of contrast (AIF). Equation (17) below relates these two parameters in a straightforward derivation that leverages the understanding of contrast advection in the coronary vessel.

Equation (17) rearranges Equation (12) and represents a one-dimensional advection equation for the cross-sectional averaged contrast concentration C which is proportional to the HU measured in CTCA:

$$\frac{\partial C}{\partial t} + \frac{Q}{A}\frac{\partial C}{\partial s} \approx 0 \Rightarrow \frac{\partial C}{\partial s} \approx -\frac{A}{Q}\left[\frac{\partial C}{\partial t}\right] \quad (17)$$

where C(t,s) is a function of time (t) and axial location (s). Assuming that Q/A changes slowly along the axial direction, the solution of Eq. (17) can be approximated as:

$$C(t,s) \approx C_{ostium}(t-As/Q) \quad (18)$$

where $C_{ostium}$ is the time variation of concentration at s=0, i.e. arterial input function (AIF). Also, integrating Eq. (17) between two axial locations $s_1$ and $s_2$ in an artery results in:

$$TAG(HU\ cm^{-1}) = \frac{C_{s_2} - C_{s_1}}{s_2 - s_1} \quad (19)$$

$$\approx -\frac{\hat{A}}{Q} \cdot \frac{\partial C}{\partial t}$$

$$\approx -\frac{\hat{A}}{Q} \cdot \frac{\partial}{\partial t}[C_{ostium}(t - \hat{A}\hat{s}/Q)]$$

where $\hat{A}$ and $\hat{s}$ are the average cross-sectional area and axial distance of the artery between the two axial locations. Thus TAG is inversely proportional to the flow rate, Q, but also related to the arterial input function, $C_{ostium}(t)$. The AIF function can be described as:

$$C_{ostium}(t) = C_{min} + \frac{1}{2}(C_{max} - C_{min})[1 - \cos(\pi(t - t_s)/T_d)] \quad (20)$$

where $C_{max}$ and $C_{min}$ are the maximum and minimum concentrations at the ostium, $t_s$ is the arrival time of the bolus, and $T_d$ is the time-delay between the arrival of the bolus and the maximum enhancement. This function provides an excellent representation of the actual time-variation of arterial enhancement illustrated in FIG. 14B. Substituting Equation (4) into Equation (3), the TAG at $t=t_s+T_d$ is estimated as:

$$TAG^*(cm^{-1}) = \frac{TAG}{C_{max} - C_{min}} \quad (21)$$

$$\sim -\frac{1}{2}\frac{\hat{A}}{Q}\frac{\pi}{T_d}\sin\left(\frac{\pi\hat{A}}{T_d Q}\hat{s}\right)$$

$$\approx -\frac{1}{2}\left(\frac{1}{Q^2}\right)\left(\frac{1}{T_d^2}\right)\pi^2\hat{A}^2\hat{s}$$

where TAG* is TAG normalized by the density rise at the ostium with units of $cm^{-1}$. Solving for Q we arrive at a simple expression for coronary flow (ml/min) as a function of TAG*, the average cross sectional area ($\hat{A}$), vessel length ($\hat{s}$) and the bolus duration $T_d$; it should also be noted that Equation (22) is derived from Equation (17).

$$Q(ml/min) = \frac{\pi\hat{A}}{T_d}\sqrt{\frac{\hat{s}}{-2(TAG^*)}} \quad (22)$$

All of the parameters in the above equation are readily available using current conventional CTA exams.

In CT angiography, the spatial resolution of the CT image is limited by the voxel size of the scanner, which for a modern multi-detector CT scanner is about 0.5 mm³. This implies for instance that the lumen of a 2 mm diameter section of a coronary artery would be resolved by only about 12 voxels, as illustrated in FIG. 13B. The voxels at the outer edges of the lumen may be partially located outside the lumen leading to errors in the estimation of the average attenuation (HU) factor at any given cross-section. This "mixing" of densities from different structures into the same voxel is known as partial volume-averaging (PVA) and is an inherent limitation for all tomographic imaging modalities.

To assess these effects in from CFD data, the simulation domain is embedded in a virtual voxel lattice and the mean attenuation value is reevaluated at a given axial location (s), as illustrated in FIG. 13D. This procedure mimics the estimation of attenuation in CTCA and $HU_{voxel}^*$ incorporates the effect of PVA inherent in these measurements. Using this approach a simple initial simulation is performed to estimate the effect of PVA and its effect on TAG for a case with area constriction of 70%, as illustrated in FIGS. 13A-13D. More particularly FIGS. 13A-13D illustrate a method for assessing partial volume averaging effect from CFD data. FIG. 13A illustrates multiple cross sectional slices in a CFD modeled coronary vessel with a decreasing luminal area. The two cross sectional views illustrated in FIGS. 13B and 13C represent simulated CT attenuation according to equations for the theoretical attenuation result considering a 0.5 mm³ voxel size without and with partial volume averaging, respectively illustrated in FIG. 13D ($Hu_{voxel}(s)$ is the mean attenuation value at a given axial location, s. $N_{lumen}$ is number of voxels covering the lumen at the axial location, s, and HUi is the average attenuation for the i-th voxel, Vi is the volume of the voxel, HU* voxel is the normalized mean attenuation value and C is the iodine concentration.) Results indicate that PVA effect combines with vessel taper to increase the measured TAG and the combination of PVA and vessel curvature/tortuosity generates spurious fluctuations in the attenuation profile. However CFD modeling which may be coupled with ex-vivo phantom studies can be used to compensate Equation (6) for PVA effects, described further, herein.

Figure 14:
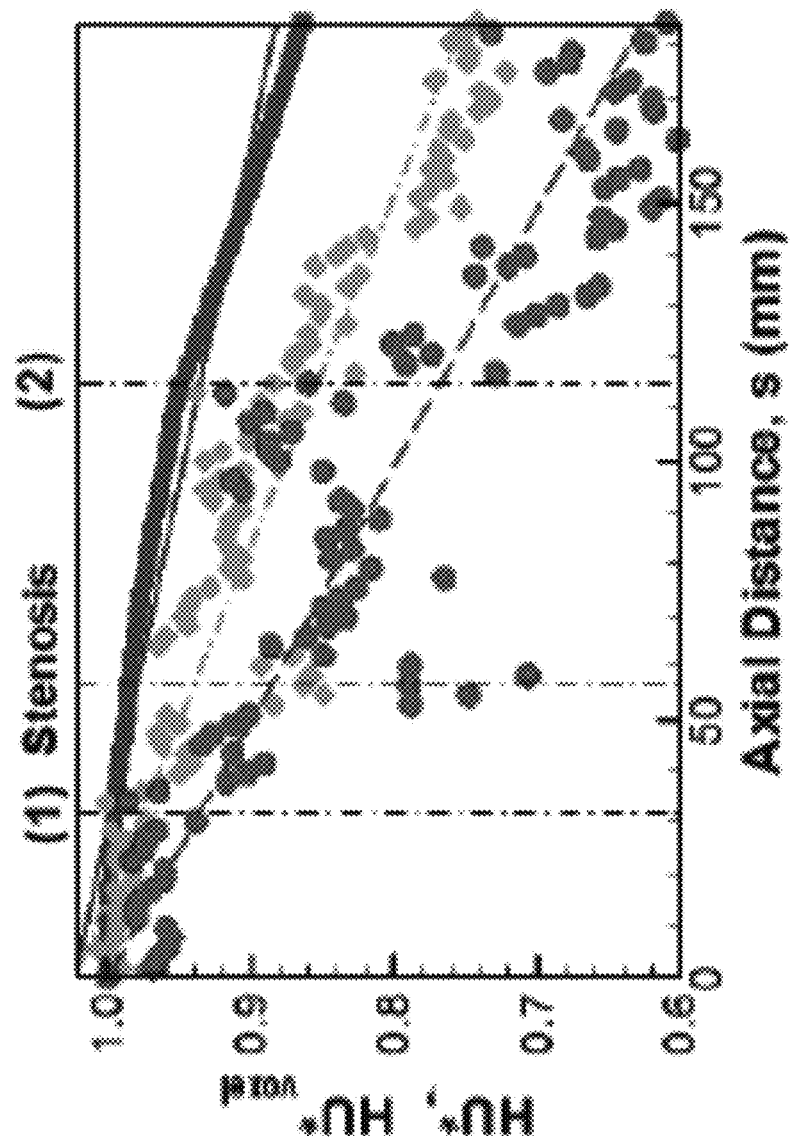
FIG. 14 illustrates a CFD simulated normalize attenuation profile for 70% area constriction for different voxel resolutions, according to an embodiment of the present invention.

FIG. 14 illustrates CFD simulated normalization attenuation profiles for 70% area constriction for voxel resolutions of 0.5 mm³, 0.25 mm³, and the case for the theoretical profile with infinite spatial resolution. Decreasing spatial resolution (increased partial volume averaging) tends to cause overestimation of TAG. To account for the artificially higher TAG values that result due to partial volume effects as shown in Figure X, a correction factors, $\delta_1$, and $\delta_2$ can be implemented that accounts for the CTA voxel resolution. From computational simulations at multiple spatial resolutions and fixed taper, $\delta_1$ is approximately equal to 3.5 for the voxel resolution used in Core 320 (approximately 0.4×0.4× 0.4 mm).

$$Q(\text{ml/min}) = \frac{\pi \hat{A}}{T_d} \sqrt{\frac{\delta_1 \hat{s}}{-2(TAG^* + \delta_2)}} \quad (23)$$

Figure 15A:
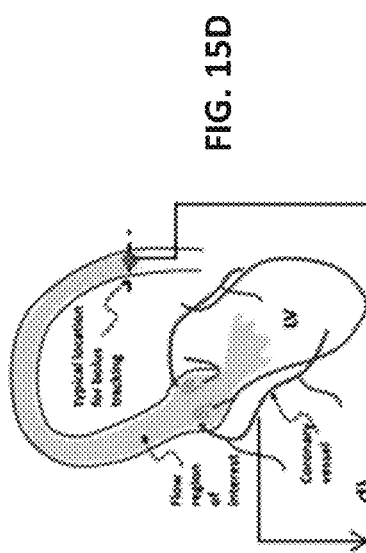
FIGS. 15A-15E illustrate a summary of the process for implementation of the current method according to an embodiment of the present invention.
Figure 15B:
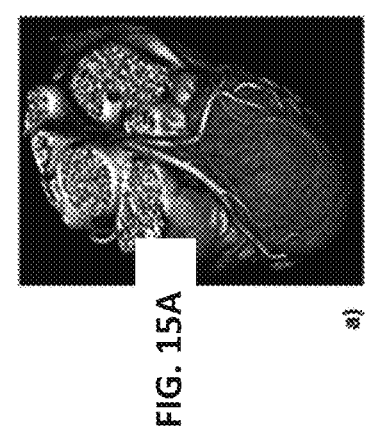
Figure 15D:
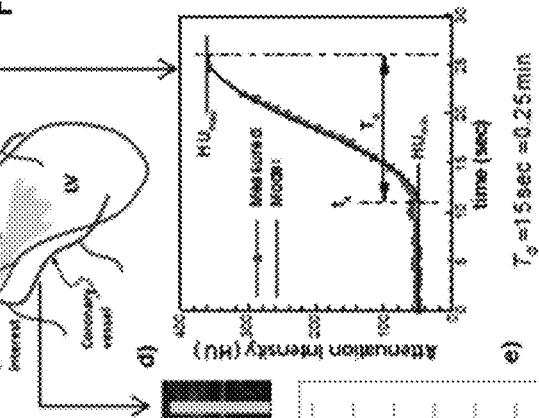
Figure 15C:
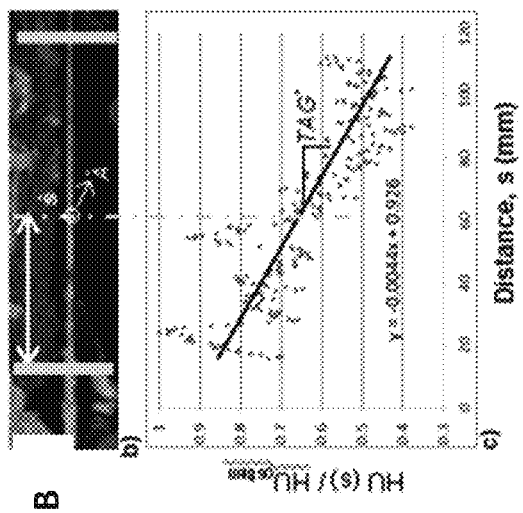
Figure 15E:
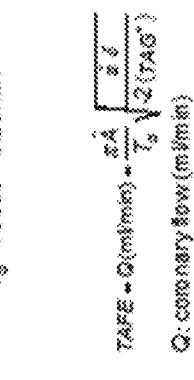

By way of example, this section will outline the process of applying Eq. 22 to real-world coronary CT angiography data for absolute coronary flow measurement in a patient with LAD disease, as illustrated in FIG. 15A-15E. As indicated in Equation (22), after the 3D CT acquisition there are a total of 4 variables that need to be extracted from the CT data for flow calculation. Three of these variables ($\hat{A}$, $\hat{s}$, TAG*) come directly from static CTCA images of the coronary vessels, as illustrated in FIGS. 15B and 15C, and one variable ($T_d$) is derived from temporal density changes following contrast injection FIGS. 15D and 15E. To summarize the process in FIGS. 15A-15E, following 3D isotemporal acquisition of the whole heart is illustrated in FIG. 15A, multiplanar reformations of the three primary coronary vessels are generated that provide a straight vessel view as illustrated in FIG. 15B. Software is then used to measure the luminal density as a function of vessel length between two user-defined proximal and distal boundary locations. The variable $\hat{s}$ is defined as the average distance between the user-defined points and $\hat{A}$ is defined as the average cross-sectional area over the length of the vessel. TAG is defined as the slope of the normalized luminal density versus distance plot, as illustrated in FIG. 15C. The temporal element of contrast dispersion needed for Equation (23) is taken from the time-density curve shown in FIG. 15E that is measured in the descending aorta, as illustrated in FIG. 15D prior to scanning to allow optimal timing or triggering of the CTA acquisition. While it is usually not used in standard CTCA, this temporal AIF data can be stored in the CT raw data and is easily reconstructed for the determination of $T_d$. Once all parameters have been isolated, Equation (23) can be used to calculate coronary flow.

In addition to CFD simulations to guide the formulation above, Equation (23) can also, for example, be used to calculate absolute coronary blood flow in an ischemic canine model of LAD stenosis and in patients with obstructive and non-obstructive coronary artery disease. However, these applications are simply examples and are not to be considered limiting.

Figure 16C:
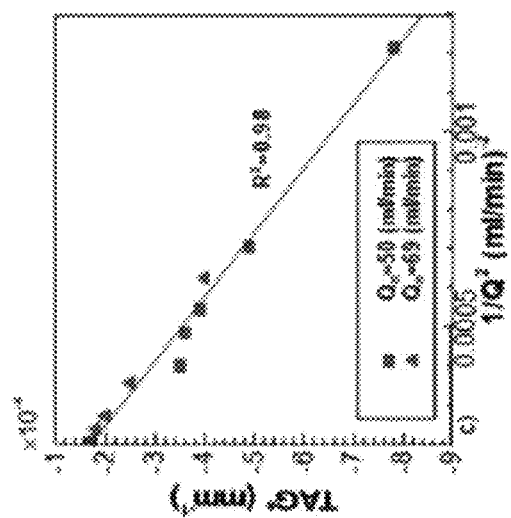
FIGS. 16A-16C illustrate the relationship between flow and TAG according to an embodiment of the present invention.
Figure 16B:
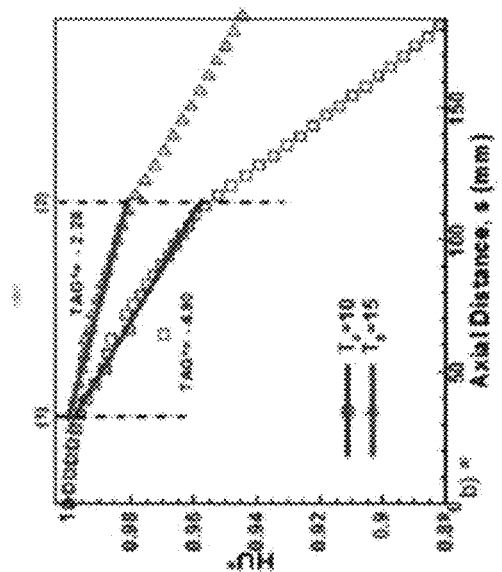
Figure 16A:
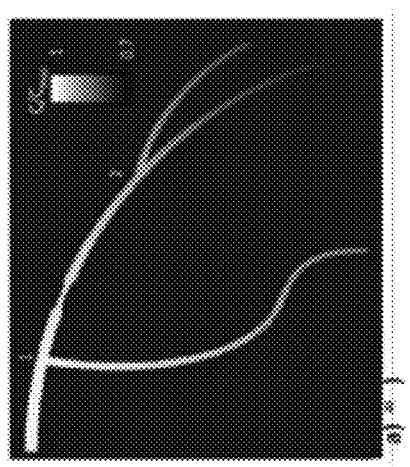

By way of another example, CFD simulations of contrast dispersion dynamics were performed in simple models of coronary artery stenosis under physiologic flow conditions to confirm the proposed relationship between TAG and AIF and the fundamental relationship between flow and TAG, as illustrated in FIGS. 16A-16C. These data demonstrate the effect of AIF pulse duration ($T_d$) on TAG and confirm the linear relationship between TAG and $1/Q^2$ detailed in Equation (21).

This data set consisted of 4 canine models of LAD stenosis that underwent CT imaging using a prototype 256-CT scanner with simultaneous microsphere injections. Despite the limited temporal resolution of this prototype scanner, image analysis and application of Equation (23) demonstrated resting coronary blood flow (LAD+LCx) of 29±10 ml/min. While coronary flow probes were not used in this study, this result is quite similar to direct probe-derived measurements in similar sized canines previously published, 31±8 ml/min.

Furthermore, there was a good correlation between flow derived from Eq. 23 and microsphere MBF (R=0.76, p<0.001). Thus, in the limited preclinical pilot data set, Equation (23) appears to provide the ability to accurately determine territorial flows supplied by the LAD and LCx and provides absolute total coronary flow values that are in agreement with those reported in the literature.

Figures 17A, 17B:
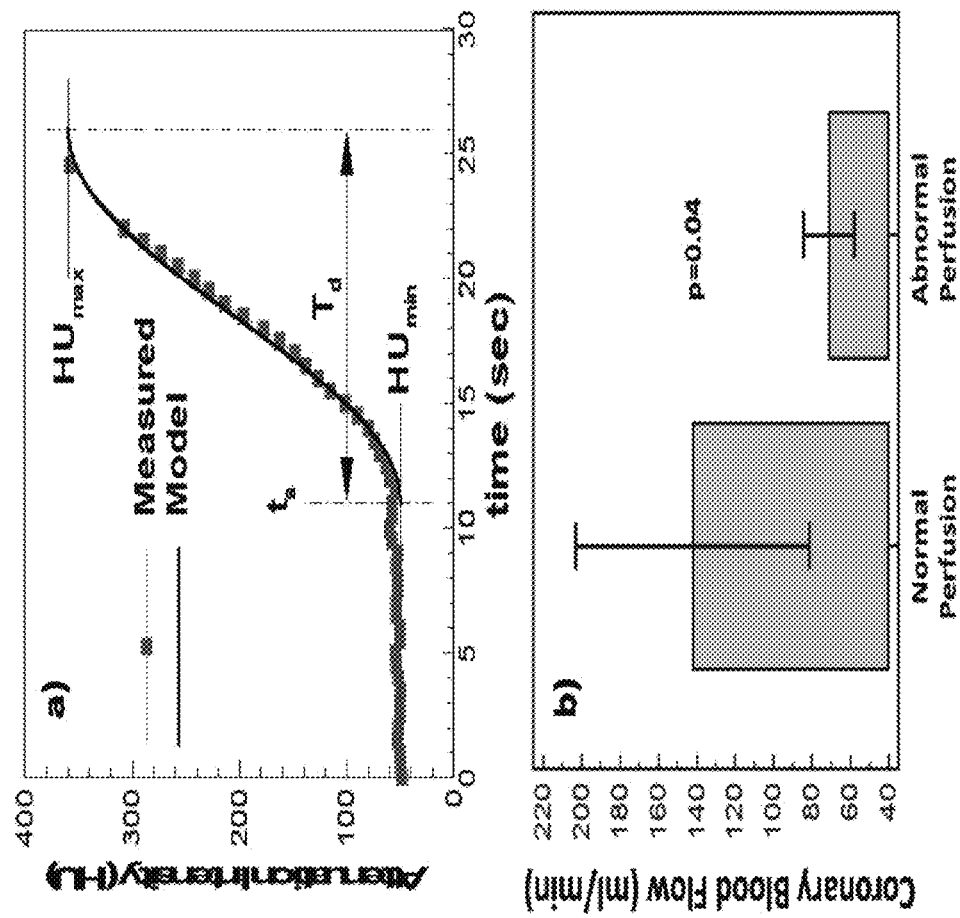
FIGS. 17A-17B illustrate graphs modeling results for specific patient data according to an embodiment of the present invention.

The clinical data set consisted of 9 patients enrolled in the CORE320 multicenter trial conducted at Johns Hopkins University. Patients in CORE320 underwent coronary CTA, stress CT and SPECT myocardial perfusion imaging. All AIF data was collected. FIG. 17A shows an AIF function for a patient included in this analysis demonstrating a perfect match of the AIF modeled in Equation (19), which gave further confidence to apply Equation (23) to the data set. Average total coronary flow (LAD+LCX+RCA) was 123.4±66 ml/min. When corrected for myocardial mass, total myocardial flow was 0.86±0.39 ml/g/min. These data are nearly identical with resting MBF seen in humans by O15-PET. When comparing patients with normal vs. abnormal perfusion by the reference standard—SPECT myocardial perfusion imaging as illustrated in FIG. 17B, TAG alone showed no significant difference between ischemic and non-ischemic territories (p=0.93). However, when TAG was normalized by the density rise at the ostium (Equation (21)) and Equation (23) applied, there was a statistically significant difference in total coronary flow, 142 ml/min vs. 71 ml/min in normal and ischemic patients, respectively (p=0.04). Results from these preliminary data in human CT studies indicate Eq. 23 accurately measures coronary blood flow and can predict myocardial perfusion abnormalities determined by SPECT; while TAG, without accounting for the AIF, cannot.

Equation (22) has been derived from highly simplified computational models and preliminary assessment of this expression against limited sets of canine and human data are highly promising and demonstrate feasibility. However, the expression can be further refined to incorporate effects of vessel tortuosity, taper and branching. In addition, there is a need to understand the effect of partial volume averaging on TAG and thus the calculation of flow using Equation (22), in both simple and more complex models. Based on the preliminary analysis, the following two corrections are hypothesized for Eq. (22).

$$Q_1(\text{ml/min}) = K(\theta; \Delta) \frac{\pi \hat{A}}{T_d} \sqrt{\frac{\hat{s}}{-2(TAG^*)}}; \quad (24)$$

$$Q_2(\text{ml/min}) = P(\hat{s}; \Delta) \frac{\pi \hat{A}}{T_d} \sqrt{\frac{\hat{s}}{-2(TAG^*)}}$$

where $Q_1$ is the measurement corrected for average vessel taper ($\theta$) and voxel dimension ($\Delta$) and $Q_2$ is the measurement corrected for local curvature and tortuosity. Multiplicative correction factor K is relatively simple since it only involves average vessel taper and voxel resolution, whereas correction factor P depends on local curvature. Note however that both correction factors K and P depend on parameters that are readily obtained from CTCA.

While FFR is considered the gold standard in assessment of coronary stenosis, the methods describe above could be applied to obtain other metrics of stenotic severity. In particular, once the pressure drop across the stenosis and the flow velocity are determined using the above method, the functional severity of the stenosis could also be determined in terms of a loss coefficient defined as $$K = \frac{\Delta P}{\left|\frac{1}{2}\rho\left(\frac{Q}{A}\right)^2\right|} \quad (25)$$

where Q is the flow rate upstream of the stenosis and A is the lumen area upstream of the stenosis. The advantage of the above measure is that it is flow-rate independent and can be obtained with a single scan at rest condition (i.e. no need for a second scan at maximal hyperemia).

A method according to the present invention provides for obtaining a patient specific transluminal attenuation gradient (TAG) over a calcium-free section of the coronary artery and determining a time variation of a contrast at a predetermined vascular or ventricular location (called the arterial input function or input bolus profile). The method also includes calculating an estimate of the fractional flow reserve (FFR) within the coronary artery using the TAG and AIF and using the FFR to determine the functional significance of the coronary artery stenosis in vessels with severe calcification. The technique can include a method for correcting the TAG values for the effects of CT spatial resolution and partial volume averaging. The technique also includes a method for correcting the TAG values for the effects of vessel tortuosity, curvature and partial volume averaging. The method can also include protocol for determining a functional significance of coronary artery stenosis includes obtaining coronary contrast concentration versus time data via a dynamic CT acquisition to calculate coronary flow velocity.

The coronary flow velocity may be obtained in the main artery as well as all of the sub branches for which contrast measurements are available. Thus, the method can provide the relative magnitude of the flow rate in the various branches and this information may be combined with other information or mathematical models to develop alternate measure of the functional significance of the coronary stenosis.

The proposed method is described herein with respect to assessment of the functional severity of constrictions in the coronary arteries. However, target anatomy need not be confined to the coronary arteries. This could be equally useful in performing assessments of other blood vessels no matter the location. Additionally, the methods need not be limited to cardiac applications. For instance, the invention can also be applied to peripheral vascular flow assessment, brain blood flow, kidney blood flow, liver blood flow, or any other blood flow assessment known to or conceivable by one of skill in the art.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for determining a functional significance of coronary artery stenosis comprising:
    obtaining image data from an imaging scan of the patient using a non-transitory computer readable medium;
    displaying the image data;
    obtaining a patient specific transluminal attenuation gradient (TAG) for the coronary artery of the patient from the image data and calculating a partial volume averaging correction factor to correct TAG values that result due to partial volume effects;
    determining an arterial input function from the imaging data, wherein the arterial input function is defined as a time variation of a contrast agent at a predetermined location in the coronary artery of the patient;
    transforming the displayed image data into a visual representation of the arterial input function using the non-transitory computer readable medium and correcting the displayed image for the partial volume effects;
    determining the coronary luminal area and distance along the artery of interest from the imaging data;
    calculating the coronary flow velocity (CFV) and flow rate within the coronary artery from an algorithm wherein terms of the algorithm are TAG, the arterial input function, the coronary luminal area and distance along the artery;
    transforming the displayed visual representation of the arterial input function into a visual representation of the CFV using the non-transitory computer readable medium;
    calculating an estimate of a pressure gradient (PG) within the coronary artery, from the coronary flow velocity, the arterial input function, information on the coronary luminal area, and position and location within the artery;
    transforming the displayed visual representation of the arterial input function into a visual representation of the PG using the non-transitory computer readable medium; and
    determining the functional significance of the coronary artery stenosis from the estimate of the PG.

2. The method of claim 1 further comprising gathering patient-specific data related to concentration of a contrast agent within a coronary artery of a patient.

3. The method of claim 1 further comprising executing the method using a non-transitory computer readable medium.

4. The method of claim 1 further comprising performing a cardiac computed tomography scan to gather the patient specific TAG.

5. The method of claim 1 wherein the patient-specific data is represented as a graph of concentration of the contrast agent over a distance in the coronary artery.

6. The method of claim 1 further comprising assessing partial volume effects in the image data by embedding a simulation domain in a virtual voxel lattice and reevaluating a mean attenuation value at a given axial location.

7. The method of claim 1 further comprising calculating flow PG and fractional flow reserve (FFR) in a vessel with calcification.

8. A method for determining a functional significance of coronary artery stenosis comprising:
    obtaining image data from an imaging scan of the patient using a non-transitory computer readable medium;
    displaying the image data;

obtaining a patient specific transluminal attenuation gradient (TAG) for the coronary artery of the patient from the image data and calculating a partial volume averaging correction factor to correct TAG values that result due to partial volume effects;

determining an arterial input function from the image data, wherein the arterial input function is defined as a time variation of a contrast agent at a predetermined location in the coronary artery of the patient;

transforming the displayed image data into a visual representation of the arterial input function using the non-transitory computer readable medium and correcting the displayed image for the partial volume effects;

calculating an estimate of the fractional flow reserve (FFR) within the coronary artery using pressure gradient (PG) estimates taken from the image data;

transforming the displayed visual representation of the arterial input function into a visual representation of the FFR using the non-transitory computer readable medium; and determining the functional significance of the coronary artery stenosis from the FFR.

9. The method of claim 8 further comprising gathering patient-specific data related to concentration of a contrast agent within a coronary artery of a patient.

10. The method of claim 8 further comprising executing the method using a non-transitory computer readable medium.

11. The method of claim 8 further comprising performing a cardiac computed tomography scan to gather the patient specific TAG.

12. The method of claim 8 wherein the patient-specific data is represented as a graph of concentration of the contrast agent over a distance in the coronary artery.

13. The method of claim 8 further comprising assessing partial volume effects in the image data by embedding a simulation domain in a virtual voxel lattice and reevaluating a mean attenuation value at a given axial location.

14. A method for determining a functional significance of coronary artery stenosis comprising:

obtaining image data from an imaging scan of the patient using a non-transitory computer readable medium, wherein the image data includes data from the patient in a state of cardiac rest and data from the patient in a state of cardiac stress;

displaying the image data;

obtaining a patient specific transluminal attenuation gradient (TAG) for the coronary artery of the patient from the image data and calculating a partial volume averaging correction factor to correct TAG values that result due to partial volume effects;

determining an arterial input function from the image data, wherein the arterial input function is defined as a time variation of a contrast agent at a predetermined location in the coronary artery of the patient;

transforming the displayed image data into a visual representation of the arterial input function using the non-transitory computer readable medium and correcting the displayed image for the partial volume effects;

calculating an estimate of the coronary flow velocity of the coronary artery using an algorithm, wherein terms of the algorithm are the patient-specific TAG, coronary luminal area, location within the coronary artery, and the arterial input function;

transforming the displayed visual representation of the arterial input function into a visual representation of the CFV using the non-transitory computer readable medium;

calculating coronary flow reserve (CFR) from the data from the patient in a state of cardiac rest and the data from the patient in a state of cardiac stress as a measure of the functional significance of the coronary artery stenosis;

transforming the displayed visual representation of the CFV into a visual representation of the CFR using the non-transitory computer readable medium;

estimating FFR from the coronary flow velocity and luminal area assessments through simplified equations;

transforming the displayed visual representation of the CFR into a visual representation of the FFR using the non-transitory computer readable medium; and estimating a loss coefficient associated with a stenosis from the data from the patient in the state of cardiac rest to determine the functional significance of the coronary artery stenosis.

15. The method of claim 14 further comprising gathering patient-specific data related to concentration of a contrast agent within a coronary artery of a patient.

16. The method of claim 14 further comprising executing the method using a non-transitory computer readable medium.

17. The method of claim 14 further comprising performing a cardiac computed tomography scan to gather the patient specific TAG.

18. The method of claim 14 wherein the patient-specific data is represented as a graph of concentration of the contrast agent over a distance in the coronary artery.

19. The method of claim 14 further using the TAG and the time gradient to calculate PG and FFR in order to determine the functional significance of the coronary artery stenosis.

20. The method of claim 14 further comprising assessing partial volume effects in the image data by embedding a simulation domain in a virtual voxel lattice and reevaluating a mean attenuation value at a given axial location.

21. The method of claim 14 further comprising correcting the flow velocity and TAG based on the taper of the vessel.

22. The method of claim 14 further comprising correcting the flow velocity and TAG based on the resolution of a computed tomography scanner.

23. The method of claim 14 further comprising correcting the flow velocity and TAG based on a curvature of the coronary artery.

24. The method of claim 14 wherein the predetermined location in the coronary artery of the patient comprises multiple predetermined locations within the coronary artery.

25. The method of claim 14 further comprising estimating coronary flow velocity (CFV) in branches of the main coronary artery and using this information to determine the functional significance of the coronary stenosis.

* * * * *